Figure 1:
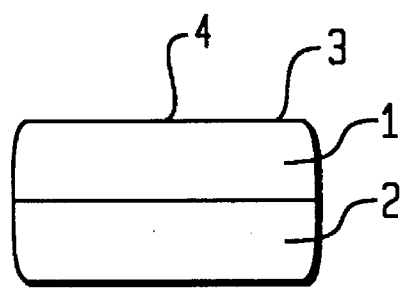

US005574011A

United States Patent [19]

Tien

[11] Patent Number: 5,574,011
[45] Date of Patent: Nov. 12, 1996

[54] COMPOSITIONS AND METHODS FOR THE TREATMENT OF MALE-PATTERN BALDNESS

[76] Inventor: Henry C. Tien, 5660 SW. 58 Pl., Miami, Fla. 33143

[21] Appl. No.: 416,190

[22] Filed: Apr. 4, 1995

[51] Int. Cl.$^6$ ..................................... A61K 37/24
[52] U.S. Cl. ................................. 514/14; 514/15
[58] Field of Search ............................. 514/14, 15

[56] References Cited

U.S. PATENT DOCUMENTS 5,362,720  11/1994  Labrie ................................. 514/169
5,434,146  7/1995   Labrie et al. ......................... 514/169

*Primary Examiner*—James H. Reamer
*Attorney, Agent, or Firm*—Olga Gonzalez, P.A.

[57] ABSTRACT

The present invention provides methods and compositions of LHRH analogs for the treatment of male-pattern baldness. Male-pattern baldness is treated by the administration of compositions containing LHRH analogs. The compositions may be administered by any of a variety of routes, including parenterally, (including subcutaneous, and intramuscular administration), topically, transdermally or transmucosally.

43 Claims, 1 Drawing Sheet

COMPOSITIONS AND METHODS FOR THE TREATMENT OF MALE-PATTERN BALDNESS

FIELD OF THE INVENTION

The present invention relates to compositions and methods for the treatment of male-pattern baldness involving analogs of luteinizing hormone-releasing hormone ("LHRH analogs"). More particularly, the LHRH analogs of the present invention may be LHRH agonists or LHRH antagonists. The LHRH analog may be administered alone or in combination with a second LHRH analog in a pharmaceutically acceptable carrier.

BACKGROUND OF THE INVENTION

Since the initial discovery of LHRH 20 years ago, roughly 5,000 LHRH analogs have been synthesized and evaluated for possible therapeutic use. However, no treatment method for male pattern baldness utilizing LHRH analogs has heretofore been advanced. The present invention is directed to the treatment of male pattern baldness with therapeutic agents known as LHRH analogs.

Male-pattern baldness, also called androgenic alopecia, is largely the result of heredity, advancing age and male hormone secretion, specifically the hormone, dihydrotestosterone. Hence, male-pattern baldness may be said to be a time dependent steroid genetic expression resulting in a diminution in the growing phase of scalp hair. In advanced stages, male-pattern baldness is characterized by a bald scalp at the crown of the head and a horseshoe shaped fringe of hair remaining on the sides of the head.

Various preparations have heretofore been proposed for the treatment of male-pattern baldness. However, these hair growth formulations are not very effective.

Minoxidil, a potent anti-hypertensive medication, has been used with limited success to regrow hair by rubbing it in lotion form into the scalp. One theory for its mode of action is that it dilates the blood vessels in order to stimulate nourishment of hair follicles. Minoxidil is not effective for the treatment of male-pattern baldness because it does not reduce the production of hormones responsible for causing male-pattern baldness. The most common side effects associated with this medication are itching and skin irritation. Moreover, Minoxidil in topical application is poorly absorbed.

Minoxidil is also inconvenient to use because patients receiving Minoxidil treatment for male pattern baldness typically must apply liquid formulations of Minoxidil to the scalp several times each day. The liquid must then be allowed to remain on the scalp for at least four hours after each application and the hair may not be washed until after the foregoing time period has elapsed. Moreover, the patient's hair must be mussed during application of Minoxidil, which does not give the patient a cosmetically pleasing appearance.

Another approach described in U.S. Pat. No. 5,183,817 is to utilize retinoids or mixtures thereof in combination with minoxidil and/or minoxidil-type compounds in stimulating or increasing the rate at which hair grows on mammalian skin. Such treatment does not reduce hormone production. It may produce itching and skin irritation. Moreover, this approach is inconvenient as it requires mussing of the hair.

Still another approach for treating male-pattern baldness has been the topical application of agents which inhibit the conversion of testosterone to dihydrotestosterone. Testosterone binds specifically to the 5α-reductase enzyme which converts testosterone to its active metabolite dihydrotestosterone (DHT). DHT eventually binds to nuclear receptor proteins and results in the synthesis of specific proteins which lead to male-pattern baldness. U.S. Pat. No. 5,053,403 discloses a method for treating male-pattern baldness through the topical application of an inhibitor of the conversion of testosterone to dihydrotestosterone by the 5α-reductase enzyme and a blocking agent which blocks the binding of dihydrotestosterone to receptor protein in cell cytoplasm. The disadvantages associated with this method are itching upon topical application, poor absorption, inconvenience in application, and the necessity of mussing of the hair. Furthermore, progesterone and progesterone-like compounds are cited as preferred inhibitors in U.S. Pat. No. 5,053,403. However, because progesterone and progesterone-like compounds do not completely inhibit the conversion of testosterone to dihydrotestosterone, such agents do not provide suitable hair growth.

An orally administered inhibitor of 5α-reductase currently in clinical trial for the treatment of male-pattern baldness is finasteride, a synthetic 4-azasteroid compound, sold under the name Proscar®. Finasteride is structurally similar to progesterone. Proscar® has been used to shrink enlarged prostates by blocking the formation of DHT. However, Proscar® does not provide an efficacious treatment of male-pattern baldness because it does not sufficiently block DHT production at the intracellular level.

Still another approach to treating male-pattern baldness has been the administration of estrogen or estrogen-based compounds, such as those disclosed in U.S. Pat. No. 5,204,337 issued to Labrie. However, the use of estrogen and estrogen-like compounds for the treatment of male-pattern baldness has not been successful because they place patients at an increased and unacceptable risk of death from cardiovascular complications, such as heart attacks, strokes, and venous thrombosis. Estrogen-like compounds also produce other undesirable side effects, such as unwanted feminization of men. This transsexual effect manifests itself in gynecomastia (enlargement of breasts) and fluid retention. Moreover, estrogen-like compounds and LHRH analogs are structurally dissimilar. Estrogen-like compounds, such as those disclosed in U.S. Pat. No. 5,204,337 have a cyclic-based structure and do not contain amino acid. By contrast, LHRH analogs are characterized by their decapeptide-based structure and contain amino acids. The LHRH analogs of the present invention are non-steroidal and do not produce the undesirable side effects associated with steroids.

The present invention provides treatments for persons suffering from male-pattern baldness which overcome the disadvantages associated with prior methods.

SUMMARY OF THE INVENTION

The present invention provides compositions and treatments in persons who are in the active phases of male pattern baldness. The active phases of male pattern baldness span the time when recession of the frontotemporal hairline begins to the period where hairline recession has run its full course. The compositions of the present invention contain LHRH analogs which suppress testosterone formation in patients suffering from male pattern baldness. The LHRH analogs may be LHRH agonists or LHRH antagonists. The common feature of every LHRH analog is a decapeptide backbone.

Agonists of LHRH either produce, emulate or mimic the effect of the naturally occurring decapeptide hormone, LHRH. Upon the administration of LHRH agonists, there is a one week transient increase in serum levels of testosterone, LH, and FSH. Subsequently, the responsiveness of the pituitary to LHRH is desensitized, resulting in decreased release of LH and FSH from the pituitary gland. Because LH and FSH stimulate the gonads to produce steroids, specifically testosterone in males, testosterone steroidogenesis is suppressed.

LHRH antagonists, however, suppress testosterone formation by blocking LH release by competitive antagonism of LHRH binding at the pituitary receptor level. Accordingly, levels of dihydrotestosterone, the hormone principally responsible for causing male pattern baldness, are also reduced.

The compositions of the present invention contain LHRH agonists, such as, Nafarelin, Leuprolide, Goserelin; Buserelin, Histrelin, Gonadorelin and others, as more specifically described herein. The compositions of the present invention may also contain LHRH antagonists such as Ganirelix, Ramorelix, Cetrovelix, Detirelix, Azaline, Antide, and others, as more specifically described herein. These LHRH analogs are well tolerated by patients and are non-toxic.

The treatment methods of the present invention involve the administration of LHRH analog compositions to patients who are in the active phases of male pattern baldness. More specifically, the LHRH analog may be administered alone or in combination with a second LHRH analog in a pharmaceutically acceptable carrier. Therefore, according to the present invention, a first LHRH agonist may be administered in combination with a second LHRH agonist; an LHRH agonist may be administered in combination with an LHRH antagonist; or a first LHRH antagonist may be administered in combination with a second LHRH antagonist.

Administration may occur through a variety of routes, such as parenteral, (including subcutaneous, and intramuscular administration), oral, topical, transdermal, transmucosal, and intranasal spray preparation. The compositions of the present invention may be administered topically to the skin under the arm pits thereby avoiding the need to affect the patient's coiffure. The compositions of the present invention may also be administered by means of depot or implant formulations. Such treatment methods involve slow release of the therapeutic agents, LHRH analogs, and avoid the disadvantage of reapplying or readministering the therapeutic agent to the patient encountered with prior methods.

DESCRIPTION OF THE INVENTION

The present invention relates to methods and compositions for treating male-pattern baldness. More specifically, the present invention provides treatment for hair loss in patients who are in the active phases of male-pattern baldness, also termed androgenic alopecia. There are generally seven types of male pattern baldness which may be categorized as summarized hereinbelow.

Type I. Type I is essentially characterized by no recession or very minimal recession along the anterior border of the hairline in the frontotemporal region.

Type II. In this type of baldness, the anterior border of the hair in the frontotemporal region has triangular areas of recession which tend to be symmetrical. These areas of denudation extend no further posteriorly than approximately 2 cm anterior to a line drawn in a coronal plane between the external auditory meatus. The hair is also thin, or sparse, along the midfrontal border of the scalp, but the area of the affected region is much less than in the frontotemporal region.

Type III. This type represents the minimal extent of hair loss considered sufficient to represent baldness. Most Type III scalps have deep frontotemporal recessions which are usually symmetrical and are either bare or very sparsely covered by hair. These recessions extend further posteriorly than a point which lies approximately 2 cm anterior to a coronal line drawn between the external auditory meatus.

Type III Vertex. In this type, the hair is lost chiefly in the vertex. There may be some frontal recession, but it does not exceed that seen in Type III. This type of baldness is most common with advancing age.

Type IV. The frontal and frontotemporal recession is more severe than in Type III. Also, there is a sparseness or absence of hair on the vertex area. These areas are extensive but separated from each other by a band of moderately dense hair that extends across the top. This band joins the fully haired fringe on each side of the head. Type IV differs from Type III Vertex in which the hair loss is primarily on the vertex.

Type V. The vertex region of alopecia remains separated from the frontotemporal region of alopecia. The separation is not as distinct, because the band of hair across the crown has become narrower and sparser. Both the vertex and frontotemporal areas of alopecia have become larger. Types V, VI, and VII are all characterized by areas of alopecia that are outlined by hair on the sides and back of the scalp, forming the shape of a horseshoe.

Type VI. In this type of baldness, the bridge of hair crossing the crown has disappeared. The frontotemporal and vertex regions of alopecia have become confluent. Moreover, the entire area of alopecia has increased laterally and posteriorly.

Type VII. Type VII is the most severe form of male pattern baldness. It is characterized by a narrow horseshoe-shaped band of hair which begins laterally just anterior to the ear and extends posteriorly on the sides and very low on the occiput. This hair is usually not dense and frequently is fine. The hair is also extremely sparse on the nape of the neck and in a semicircle above both ears. Another characteristic is that the anterior border of the band on each side of the head has receded posteriorly to just in front of the ears.

There are also "Type A Variant" male pattern baldness which may be described and categorized as follows. Type A Variant is distinguished by two major features and two minor features. The major features listed below must be present to make the Type A designation. The minor features listed below are not necessary but frequently are present.
Major Features
(1) The entire anterior border of the hairline progresses posteriorly without leaving the usual island or peninsula of hair in the midfrontal region.
(2) There is no simultaneous development of a bald area on the vertex. Instead, the anterior recession advances progressively posteriorly to the vertex.
Minor Features
(1) Scattered sparse hairs frequently persist in the entire area of denudation.
(2) The horseshoe-shaped fringe of hair that remains on the sides and back tends to be wider and reach higher on the head.

Type II A. The entire anterior border of the hairline lies high on the forehead. The usual midfrontal peninsula or island of hair is represented only by a few sparse hairs. The area of denudation extends no further than 2 cm from the midfrontal line.

Type III A. The are of denudation is almost to or may actually reach the midcoronal line.

Type IV A. The area of alopecia passes the midcoronal line. There may be a considerable amount of thinning posterior to the actual hairline.

Type V A. This is the most advanced degree of alopecia described with this variant. If it becomes more extensive, it cannot be distinguished from the usual Type V and VI. The area of alopecia has not reached the vertex.

There are also other types of androgenic alopecia. The common feature of all these types of alopecia is that, instead of the areas involved becoming totally bald, they seem to reach a certain point of decreased density after which further progress is barely perceptible.

For example, in "diffuse, unpatterned alopecia," there is a general decrease in the density of hair without any definite pattern, although it is usually more marked over the top and front. This type of baldness is common in women.

The hair loss patterns in "diffuse, patterned alopecia" are essentially the same as more common male pattern baldness, but the areas involved do not become totally bald. The hair only decreases in density. This type of baldness also occurs in women.

"Male pattern baldness with persistent midfrontal forelock" can be of any degree of severity, but is characterized by a persistence of the midfrontal forelock.

"Senile Alopecia" occurs in all scalps, male and female, with age. The decrease in density involves not just the top and sides, but the entire scalp.

By "active phases" of male pattern baldness, it is meant the first instance when recession of the frontotemporal hairline begins, which is generally represented by Type I, to a period where hairline recession has run its full course, which is generally represented by Type VII. As used herein "active phases" is meant to include all types of baldness described hereinabove, including the variant types, such as diffuse unpatterned alopecia, diffuse patterned alopecia, persistent midfrontal forelock and senile alopecia. The degree and extent of balding which ultimately develops varies from individual to individual and is dependent on hereditary factors, also termed the family pedigree. Hence, the present invention is directed to treatments which can begin any time after frontotemporal hairline recession develops to a time just before the ultimate type which the family pedigree dictates. Furthermore, the treatment methods of the present invention are suitable for use in men, as well as women.

The compositions of the present invention act to suppress testosterone formation in patients suffering from male-pattern baldness. The decrease of testosterone levels in such patients results in a concomitant decrease in levels of dihydrotestosterone, which as explained hereinabove, is the hormone principally responsible for the synthesis of specific proteins that cause male-pattern baldness.

Luteinizing Hormone-Releasing Hormone (or "LHRH"), as referred to herein, is a peptide hormone released from the hypothalamus which acts on the pituitary gland to cause release of Luteinizing Hormone ("LH") and Follicle Stimulating Hormone ("FSH"). The chemical formula of LHRH may be expressed as follows:

(pyro)
Glu—His—Trp—Ser—Tyr—Gly—Leu—Arg—Pro—Gly—NH$_2$
 1     2    3    4    5    6    7    8    9    10

LH and FSH subsequently stimulate the gonads to produce steroids, specifically testosterone in males. LHRH is often referred to in the art as Gonadotropin-Releasing Hormone or GnRH. As used herein, the term "LHRH" is inclusive of GnRH. As used herein, the term LHRH analog is intended to mean a chemical compound which is similar in structure to that of LHRH. The numbers shown below the amino acid residues of the LHRH structure shown above, refer to the position of the amino acid.

As used herein, the term "LHRH agonist" means an agent which either produces, emulates, or mimics the effect of the naturally occurring endogenous LHRH peptide released from the hypothalamus and which causes a therapeutically effective decrease in the release of LH and FSH from the pituitary gland. Therefore, the LHRH agonist desensitizes the responsiveness of the pituitary to LHRH, which in turn causes a reduction in testosterone formation.

By contrast, LHRH antagonists are agents which through a competitive binding mechanism inhibit or neutralize the effect of the naturally occurring LHRH when in the presence of such endogenous hormone. Hence, the LHRH antagonists block the LHRH receptor by a competitive binding mechanism.

There are two main advantages of using LHRH analogs in the treatment of male-pattern baldness; they are well tolerated by patients and are non-toxic even in overdosing quantities. Moreover, any side effects produced by LHRH analogs are completely reversible upon discontinuation of therapy.

The LHRH analogs suitable for the practice of the present invention are of the general chemical structures shown hereinbelow in Table I (LHRH Agonists) and Table II (LHRH Antagonists). Suitable LHRH analogs are synthetic versions of the naturally occurring LHRH which contain a slightly different amino acid sequence (with various side chains attached to the amino acids) or wherein some of the naturally occurring amino acids have been eliminated.

TABLE I (LHRH Agonists)

pGlu—His—Trp—Ser—Tyr—A—Leu—Arg—Pro—Gly—NH$_2$ $$\text{pGlu—His—Trp—Ser—Tyr—A}\overset{\overset{R^1}{|}}{-}\text{Leu—Arg—Pro—Gly—NH}_2$$

pGlu—His—Trp—Ser—Tyr—A—Leu—Arg—Pro—B—NH$_2$ pGlu—His—Trp—Ser—Tyr—A—Leu—Arg—Pro—NHR$^2$ $$\text{pGlu—His—Trp—Ser—Tyr—A}\overset{\overset{R^1}{|}}{-}\text{Leu—Arg—Pro—B—NH}_2$$

$$\text{pGlu—His—Trp—Ser—Tyr—A}\overset{\overset{R^1}{|}}{-}\text{Leu—Arg—Pro—NHR}^2$$

$$\text{pGlu—His—Trp—Ser—Tyr—Gly}\overset{\overset{R^1}{|}}{-}\text{C—Arg—Pro—NHEt}$$

$$\text{pGlu—His—Trp—Ser—Tyr—Gly}\overset{\overset{R^1}{|}}{-}\text{C—Arg—Pro—NHR}^2$$

pGlu—His—Trp—Ser—Tyr—A—B—Arg—Pro—Azgly—NHR$^2$ $$\text{pGlu—His—Trp—Ser—Tyr—A}\overset{\overset{R^1}{|}}{-}\text{B}\overset{\overset{R^2}{|}}{-}\text{Arg—Pro—Azgly—NHR}^2$$

pGlu—His—Trp—Ser—Tyr—A—Lev—Arg—Pro—B—NHR$^2$

TABLE I-continued (LHRH Agonists)

$$\text{pGlu—His—Trp—Ser—Tyr—A—Lev—Arg—Pro—B—NHR}^2 \text{ with } R^1$$

Where, (1) pGlu may also be 5-oxoPro.
(2) A may be any amino acid, including B.

A D-amino acid in "A" coupled with a $Pro^9$-NHEt substitution (to replace the Gly residue), provides the most potent agonists. The more hydrophilic aza-Gly (—NH—NH—CO—$NH_2$) substitution resists proteolysis and gives high potency agonists. As used herein, the term "potency" refers to the strength of activity of the LHRH analog relative to the strength of activity of naturally occurring LHRH. The potency of the analogs of the present invention may be 10 to 200 or more times that of naturally occurring LHRH.

There is a parabolic correlation between the electronic parameters of substitutents in position "A" and potency, with a certain optimum hydrophobicity giving the most potent agonists. However, this relationship is not rigid and, for example, isolipophilic agonists [D-Nal(2)$^6$] LHRH and [D-Nal(1)$^6$] LHRH may have substantially different potencies.

The potency of LHRH agonists is also maximized by substitutions of "A" which facilitate formation of a β-bend structure. A D-amino acid in position "A" sufficiently stabilizes the β-bend conformation which is the receptor-bound conformation of LHRH agonists.

(3) B may be any amino acid, including A. Exemplary of A and B are: Tyr, Ser, Phe, Ala, aza-Gly, —NH—NH—CO—$NH_2$, NH—NH—CO—, azgly, and any other amino acid.

(4) $R^1$ may be any side chain, including H and $R^2$. Exemplary of $R^1$ are: H, —$CH_2$—O—$Bu^t$, —$CH(CH_3)$—O—$BU^t$, —$CH_2$—S—$Bu^t$, and others.

Another structural factor for achieving increased LHRH analog potencies is the presence of lipophilic side-chains at position "$R^1$" of D-amino acids in position "A". An increased local lipophilicity is also achieved by substituting ethyl amide for 10-glycine, which enhances potency five fold. This lipophilic side-chain requirement is necessary for proper fit of the LHRH agonist to the receptor site.

(5) $R^2$ may be any branch, including H and $R^1$. Examples of $R^2$ are: Et, Ethyl, Me, $BU^t$, and other N-methylation.
(6) C may be A ($Bu^t$)
   Exemplary of C are: Cys($Bu^t$), Tyr($Bu^t$), Phe($Bu^t$), and Ala ($BU^t$).
(7) Nitrogen at position 11 may also be replaced by phosphorous, sulfur or carbon for all the chemical structures shown above.

TABLE II (LHRH Antagonists)

$$\text{D—E—F—Ser—G—H—I—J—Pro—K—NH}_2 \text{ (or NH) with D' E' F' G' H' I' J' K'}$$

Where,

D may be any amino acid, including Ac-D-Nal(2), pGlu, Ac-Δ3Pro, N-Ac-pCl-Phe, Ac-D-Phe, or Ac-Pro.
D' may be any side chain, including H, Ac, or Cl.
E may be any amino acid, including His, Phe, D-pCl-Phe, D-Phe (4Cl), 4F-D-Phe, D-pF-Phe, or D-Cpa.
E' may be any side chain, including H, pCl, pF, 4Cl, or 4F.
F may be any amino acid, including Trp, D-Trp, or D-Pal.
F' may be any side chain or side group, including H.
G may be any amino acid, including Tyr, Arg, hArg, Pal, hArg $(Et)_2$, hArg (Bu), Lys, Lys (Atz), Aph, Aph (Atz), or Nic Lys.
G' may be any side chain or side group, including H, $Et_2$, Bu, Atz, or Nic.
H may be any amino acid, including Gly, Arg, D-hArg($Me_2$), D-hArg($Et_2$), D-hArg($Pr_2$), D-Phe, D-Trp, D-Lys, D-Pal, D-Tyr, D-Glu, Cit, D-Lys (Atz), Aph, or Aph (Atz).
H' may be any side chain or side group, including H, [$A_2$ pr $(Ac)_2$], [$A_2$ pr $(For)_2$] [$A_2$ bu $(For)_2$], [$A_2$ bu $(Prl)_2$], [$A_2$ pr (Et Car)$_2$] [$A_2$ pr $(CHC)_2$], [$A_2$ bu $(Car)_2$], [$A_2$ pr $(Bz)_2$], [$A_2$ bu $(AC)_2$], [$A_2$ bu $(CHC)_2$], [$A_2$ bu $(LAU)_2$], [$A_2$ pr $(Car)_2$], $(CH_2)_3$, $(Et)_2$, Bu, $(CH_2 CF_3)_2$, Atz, or Nic.

Where,
   Car=carbomoyl,
   For=formyl, Prl=propionyl,
   CHC=cyclohexyl carbonyl, Bz=benzoyl,
   $A_2$pr=2, 3- diaminoprionic acid,
   $A_2$bu=2.4- diaminobutyric acid,
   LAU=lauroyl.

I may be any amino acid, including Leu, or Phe.
I' may be any side chain or side group, including H.
J may be any amino acid, including Arg, hArg($Et_2$), hArg $(CH_2)_3$, hArg($CH_2 CF_3)_2$, hArg (Bu), Lys, ELys, or Ilys.
J' may be any side chain or side group, including H, $Et_2$, $(CH_2)_3$, $(CH_2 CF_3)_2$, or Bu.
K may be any amino acid, including Gly, D-Ala, D-Arg, or Az Gly.
K' may be any side chain or side group, including H, or Az.

While not inclusive of all the LHRH analogs suitable for the practice of the present invention, the preferred LHRH analogs according to the present invention are shown hereinbelow. Table III shows preferred LHRH Agonists and Table IV shows preferred LHRH Antagonists. Superscripts in the formulas shown in these Tables denote the position along the LHRH decapeptide where the substitute residue is found.

TABLE III

(LHRH Agonists)

Nafarelin
5-oxoPro—His—Trp—Ser—Tyr—N---C---C—Leu—Arg—Pro—Gly—NH$_2$ or [D-Nal(2)$^6$] LHRH
(with H, CH$_2$, O substituents on the central C, and naphthalene attached via CH$_2$)

Leuprolide
5-oxoPro—His—Trp—Ser—Tyr—D—Leu—Leu—Arg—Pro—NHC$_2$H$_5$

Goserelin
5-oxoPro—His—Trp—Ser—Tyr—D—Ser(t-Bu)-Leu—Arg—Pro—NHNHCONH$_2$

Buserelin
5-oxoPro—His—Trp—Ser—Tyr—D—Ser(t-Bu)-Leu—Arg—Pro—NHC$_2$H$_5$

Histrelin
5-oxoPro—His—Trp—Ser—Tyr—N$^t$-benzyl-His—Leu—Arg—Pro—NHC$_2$H$_5$

Gonadorelin
5-oxoPro—His—Trp—Ser—Tyr—Gly—Leu—Arg—Pro—Gly—NH$_2$

[D—Gly(—CH$_2$—S—Bu$^t$)$^6$, Pro$^9$—NHEt] LHRH
[D—Ser(Bu$^t$)$^6$, Pro$^9$—NHEt] LHRH
[D—Gly(—CH$_2$—O—Bu$^t$)$^6$, Pro$^9$—NHEt] LHRH
[D—Gly(—H)$^6$, Cys(Bu$^t$)$^7$, Pro$^9$—NHEt] LHRH
[D—Gly—(—CH$_2$—O—Bu$^t$)$^6$, Cys(Bu$^t$)$^7$, Pro$^9$—NHEt] LHRH
[D—Tmo$^6$] LHRH
[D—Trp$^6$, Pro$^9$—NHEt] LHRH
[D—Cha$^6$] LHRH
[D—Pfp$^6$] LHRH
[D—Nal(1)$^6$] LHRH
[D—Nal(2)$^6$] LHRH
[D—Mtf$^6$] LHRH
[D—Ptf$^6$] LHRH
[D—Tmp$^6$] LHRH
[D—Arg$^6$] LHRH
[D—Arg$^6$, Pro$^9$—NHEt] LHRH
[D—hArg$^6$ (Et$_2$)$^6$, Pro$^9$—NHEt] LHRH
[D—Dca$^6$] LHRH
[D—Phe$^6$] LHRH
[D—Ser(Bu$^t$)$^6$, Azgly$^{10}$] LHRH
[D—Nal(2)$^6$, aza—Gly$^{10}$] LHRH
[D—Nal(2)$^6$] LHRH
[D—Nal(2)$^6$, Pro$^9$—NHEt] LHRH
[D—Ser(Bu$^t$)$^6$, aza—Gly$^{10}$] LHRH
[D—Trp$^6$] LHRH
[D—Trp$^6$, Pro$^9$—NHEt] LHRH
[D—His(Bzl)$^6$, Pro$^9$—NHEt] LHRH
[D—Nal(2)$^6$, aza—Gly$^{10}$] LHRH Where [D-Nal(2)$^6$] represents:

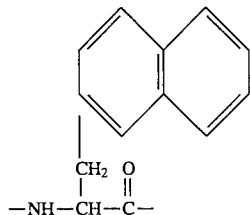

50

—NH—CH—C—
      |    ||
      CH$_2$  O

55

TABLE IV

(LHRH Antagonists)

N$^G$, N$^{G'}$-dialkyl-D-homoarginines
[N—Ac—D—Nal(2)$^1$, D—pCl—Phe$^2$, D-Trp$^3$, D—hArg(Et$_2$)$^6$, D—Ala$^{10}$] LHRH
[N—Ac—D—Nal(2)$^1$, D—pClPhe$^2$, D—Pal(3)$^3$, D—hArg(Et$_2$)$^6$, L—hArg(Et$_2$)$^8$, D—Ala$^{10}$] LHRH, also known as Ganirelix or RS-26306

TABLE IV-continued (LHRH Antagonists)

[Ac—D—Nal(2)—D—pCl—Phe—D—Trp—Ser—Tyr—D—Ser(Rha)—Leu—Arg—Pro—AzGly—NH$_2$] LHRH,
also known as Ramorelix or HOEO13
(Ac—D—Nal(2)$^1$, D—Phe(4Cl)$^2$, D—Pal(3)$^3$, D—Cit$^6$, D—Ala$^{10}$) LHRH,
also known as Cetrorelix or SB-75
Nal—Glu (Ac—D—Nal(2)1, D—Phe(4Cl)2, D—Pal 3, Arg5, D-Glu$^6$ (AA), D—Ala$^{10}$)
(Ac—D—Nal(2)$^1$, D—pCl—Phe$^2$, D—Trp$^3$, D—hArg(Et2)$^6$, D—Ala$^{10}$),
also known as Detirelix
(Ac—Δ3Pro!, 4F—D—Phe2, D—Trp3, 6) or 4F
(Ac—DNal—DCpa—DPal—Ser—Arg—D-2-amino-5-oxo-5-(4-methoxyphenol) pentanoic
acid-Leu—Arg—Pro—DAla—NH$_2$), also known as "Nal—Glu"
[Ac—DNal$^1$, DCpa$^2$, Dpal$^3$, Lys$^5$(Atz), DLys$^6$ (Atz), ILys$^8$, DAla$^{10}$] LHRH,
also known as Azaline
[Ac—DNal$^1$, DCpa$^2$, DPal$^3$, Aph$^5$(Atz), DAph$^6$(Atz), ELys$^8$, DAla$^{10}$] - LHRH,
also known as Azaline B
[N—Ac—D-2-Nal$^1$, DpClPhe$^2$, D-3-Pal$^3$, NicLys$^5$, D—NicLys$^6$, ILys$^8$, D—Ala$^{10}$] LHRH,
also known as Antide
[N—Ac—D-2-Nal$^1$, D—Phe$^2$, D-3-Pal$^3$, NicLys$^5$, D—NicLys$^6$, ILys$^8$, D—Ala$^{10}$] LHRH
[N—Ac—D—Nal(2)$^1$, D—pF—Phe$^2$, D—Trp$^3$, D—Arg$^6$] GnRH
[N—Ac—D—Nal(2)$^1$, D—pCl—Phe$^2$, D—Pal(3)$^3$, Arg$^5$, D—Glu(AA)$^6$, D—Ala$^{10}$] GnRH
[N—Ac—D—Nal(2)$^1$, D—pCl—Phe$^2$, D—Trp$^3$, D—hArg(Et)$_2$$^6$, D—Ala$^{10}$] GnRH (detirelix)
[N—Ac—D—Nal(2)$^1$, D—pCl—Phe$^2$, D—Pal(3)$^3$, D—hArg(Et)$_2$$^6$, Phe$^7$, D—Ala$^{10}$] GnRH
[N—Ac—D—Nal(2)$^1$, D—pCl—Phe$^2$, D—Trp$^3$, D—hArg(CH$_2$)$_3$$^6$, D—Ala$^{10}$] GnRH
[N—Ac—D—Nal(2)$^1$, D—pCl—Phe$^2$, D—Pal(3)$^{3,6}$, Arg$^5$, hArg(Et)$_2$$^8$, D—Ala$^{10}$] GnRH
[N—Ac—D—Nal(2)$^1$, D—pCl—Phe$^2$, D—Pal(3)$^{3,6}$, Arg$^5$, hArg(CH$_2$)$_3$$^8$, D—Ala$^{10}$] GnRH
[N—Ac—D—Nal(2)$^1$, D—pF—Phe$^2$, D—Pal(3)$^{3,6}$, Arg$^5$, hArg(CH$_2$)$_3$$^8$, D—Ala$^{10}$] GnRH
[N—Ac—D—Nal(2)$^1$, D—pCl—Phe$^2$, D—Pal(3)$^{3,6}$, Arg$^5$, hArg(CH$_2$CF$_3$)$_2$$^8$, D—Ala$^{10}$] GnRH
[N—Ac—D—Nal(2)$^1$, D—pCl—Phe$^2$, D—Trp$^{3,6}$, Arg$^5$, hArg(CH$_2$)$_3$$^8$, D—Ala$^{10}$] GnRH
[N—Ac—D—Nal(2)$^1$, D—pCl—Phe$^2$, D—Trp$^{3,6}$, Arg$^5$, hArg(CH$_2$CF$_3$)$_2$$^8$, D—Ala$^{10}$] GnRH
[N—Ac—D—Nal(2)$^1$, D—pF—Phe$^2$, D—Pal(3)$^{3,6}$, hArg(Et)$_2$$^{5,8}$, D—Ala$^{10}$] GnRH
[N—Ac—D—Nal(2)$^1$, D—pCl—Phe$^2$, D—Pal(3)$^{3,6}$, hArg(Bu)$^{5,8}$, D—Ala$^{10}$] GnRH
[N—Ac—D—Nal(2)$^1$, D—pCl—Phe$^2$, D—Pal(3)$^3$, D—Tyr$^6$, hArg(CH$_2$CF$_3$)$_2$$^{5,8}$, D—Ala$^{10}$] GnRH
[N—Ac—D—Nal(2)$^1$, D—pCl—Phe$^2$, D—Pal(3)$^{3,6}$, hArg(Et)$_2$$^8$, D—Ala$^{10}$] GnRH
[N—Ac—D—Nal(2)$^1$, D—pCl—Phe$^2$, D—Pal(3)$^{3,6}$, hArg(CH$_2$)$_3$$^8$, D—Ala$^{10}$] GnRH
[N—Ac—D—Nal(2)$^1$, D—pCl—Phe$^2$, D—Pal(3)$^{3,6}$, hArg(Bu)$^8$, D—Ala$^{10}$] GnRH
[N—Ac—D—Nal(2)$^1$, D—pCl—Phe$^2$, D—Pal(3)$^{3,6}$ Pal(3)$^5$, hArg(CH$_2$CF$_3$)$_2$$^8$, D—Ala$^{10}$] GnRH
[N—Ac—D—Nal(2)$^1$, D—pCl—Phe$^2$, D—Trp$^{3,6}$, hArg(Et)$_2$$^8$, D—Ala$^{10}$] GnRH
[N—Ac—D—Nal(2)$^1$, D—pCl—Phe$^2$, D—Trp$^{3,6}$, hArg(CH$_2$)$_3$$^8$, D—Ala$^{10}$] GnRH
[N—Ac—D—Nal(2)$^1$, D—pCl—Phe$^2$, D—Trp$^{3,6}$, hArg(Bu)$^8$, D—Ala$^{10}$] GnRH
[N—Ac—D—Nal(2)$^1$, D—pCl—Phe$^2$, D—Trp$^{3,6}$, hArg(CH$_2$CF$_3$)$_2$$^8$, D—Ala$^{10}$] GnRH
[N—Ac—D—Nal(2)$^1$, D—pCl—Phe$^2$, D—Pal(3)$^3$, D—hArg(Et)$_2$$^6$, hArg(Et$_2$)$^8$, D—Ala$^{10}$] GnRH (ganirelix)
[N—Ac—D—Nal(2)$^1$, D—pCl—Phe$^2$, D—Pal(3)$^3$, D—hArg(CH$_2$)$_3$$^6$, hArg(CH$_2$)$_3$$^8$, D—Ala$^{10}$] GnRH
[N—Ac—D—Nal(2)$^1$, D—pCl—Phe$^2$, D—Pal(3)$^3$, D—hArg(Bu)$^6$, hArg(Bu)$_1$$^8$, D—Ala$^{10}$] GnRH
[N—Ac—D—Nal(2)$^1$, D—pF—Phe$^2$, D—Pal(3)$^3$, D—hArg(Et)$_2$$^6$, hArg(Et)$_2$$^8$, D—Ala$^{10}$] GnRH
[N—Ac—D—Nal(2)$^1$, D—pF—Phe$^2$, D—Pal(3)$^3$, D—hArg(Bu)$^6$, hArg(CH$_2$CF$_3$)$_2$$^8$, D—Ala$^{10}$] GnRH
[N—Ac—D—Nal(2)$^1$, D—pF—Phe$^2$, D—Pal(3)$^3$, D—hArg(CH$_2$CF$_3$)$_2$$^6$, hArg(Et)$_2$$^8$, D—Ala$^{10}$] GnRH
[N—Ac—D—Nal(2)$^1$, D—pCl—Phe$^2$, D—Trp$^3$, D—hArg(Et)$_2$$^6$, hArg(Et)$_2$$^8$, D—Ala$^{10}$] GnRH
[N—Ac—D—Nal(2)$^1$, D—pCl—Phe$^2$, D—Trp$^3$, D—hArg(CH$_2$)$_3$$^6$, hArg(CH$_2$)$_3$$^8$, D—Ala$^{10}$] GnRH
Ac—D—Na(2) D—Phe—(4Cl) D—Pal(3) Ser Tyr D—Lys(A$_2$pr(Ac)$_2$) Leu Arg Pro D—Ala—NH$_2$
Ac—D—Na(2) D—Phe—(4Cl) D—Pal(3) Ser Tyr D—Lys(A$_2$pr(For)$_2$) Leu Arg Pro D—Ala—NH
Ac—D—Na(2) D—Phe—(4Cl) D—Pal(3) Ser Tyr D—Lys(A$_2$bu(For)$_2$) Leu Arg Pro D—Ala—NH$_2$
Ac—D—Na(2) D—Phe—(4Cl) D—Pal(3) Ser Tyr D—Lys(A$_2$bu(Prl)$_2$) Leu Arg Pro D—Ala—NH
Ac—D—Na(2) D—Phe—(4Cl) D—Trp Ser Arg D—Lys(A$_2$pr(For)$_2$) Leu Arg Pro D—Ala—NH
Ac—D—Na(2) D—Phe—(4Cl) D—Pal(3) Ser Tyr D—Lys(A$_2$pr(EtCar)$_2$) Leu Arg Pro D—Ala—NH
Ac—D—Na(2) D—Phe—(4Cl) D—Pal(3) Ser Tyr D—Lys(A$_2$pr(CHC)$_2$) Leu Arg Pro D—Ala—NH
Ac—D—Na(2) D—Phe—(4Cl) D—Pal(3) Ser Tyr D—Lys(A$_2$bu(Car)$_2$) Leu Arg Pro D—Ala—NH
Ac—D—Na(2) D—Phe—(4Cl) D—Pal(3) Ser Tyr D—Lys(A$_2$pr(BZ)$_2$) Leu Arg Pro D—Ala—NH
Ac—D—Na(2) D—Phe—(4Cl) D—Pal(3) Ser Tyr D—Lys(A$_2$bu(Ac)$_2$) Leu Arg Pro D—Ala—NH
Ac—D—Na(2) D—Phe—(4Cl) D—Pal(3) Ser Tyr D—Lys(A$_2$bu(CHC)$_2$) Leu Arg Pro D—Ala—NH
Ac—D—Na(2) D—Phe—(4Cl) D—Pal(3) Ser Tyr D—Lys(A$_2$bu(LAU)$_2$) Leu Arg Pro D—Ala—NH
Ac—D—Na(2) D—Phe—(4Cl) D—Pal(3) Ser Tyr D—Lys(A$_2$pr(Car)$_2$) Leu Arg Pro D—Ala—NH
[N—Ac—D—pCl—Phe$^1$, D—pCl—Phe$^2$, D—Trp$^3$, D—Arg$^6$, D—Ala$^{10}$]LHRH
[N—Ac—D—Nal(2)$^1$, D—pF—Phe$^2$, D—Trp$^3$, D—Arg$^6$]LHRH
[N—Ac—D—pCl—Phe$^1$, D—pCl—Phe$^2$, D—Trp$^3$, D—hArg(Me$_2$)$^6$, D—Ala$^{10}$]LHRH
[N—Ac—D—Nal(2)$^1$, D—pF—Phe$^2$, D—Trp$^3$, D—hArg(Me$_2$)$^6$]LHRH
[N—Ac—D—pCl—Phe$^1$, D—pCl—Phe$^2$, D—Trp$^3$, D—hArg(Et$_2$)$^6$, D—Ala$^{10}$]LHRH
[N—Ac—D—pCl—Phe$^1$, D—pCl—Phe$^2$, D—Trp$^3$, D—hArg(Et$_2$)$^6$]LHRH
[N—Ac—D—Nal(2)$^1$, D—pF—Phe$^2$, D—Trp$^3$, D—hArg(Et$_2$)$^6$]LHRH
[N—Ac—D—Nal(2)$^1$, D—pCl—Phe$^2$, D—Trp$^3$, D—hArg(Et$_2$)$^6$]LHRH
[N—Ac—D—Nal(2)$^1$, D—pCl—Phe$^2$, D—Trp$^3$, D—hArg(Et$_2$)$^6$, D—Ala$^{10}$]LHRH
[N—Ac—D—pCl—Phe$^1$, D—pCl—Phe$^2$, D—Trp$^3$, D—hArg(Pr$_2$)$^6$, D—Ala$^{10}$]LHRH
[N—Ac—D—pCl—Phe$^1$, D—pCl—Phe$^2$, D—Trp$^3$, D—hArg(Pr$_2$)$^6$]LHRH
[N—Ac—D—Nal(2)$^1$, D—pF—Phe$^2$, D-Trp$^3$, D—hArg(Pr$_2$)$^6$LHRH
[D—Phe$^2$] LHRH
[D—Phe$^{2,6}$] LHRH
[Ac—Pro$^1$, D—Phe$^2$, D—Trp$^6$] LHRH
[Ac—D—Phe$^1$, D—(pCl)Phe$^2$, D—Trp$^{3,6}$] LHRH
[Ac—Δ$^3$Pro$^1$, D—(pF)Phe$^2$, D—Trp$^{3,6}$] LHRH

TABLE IV-continued (LHRH Antagonists)

[Ac—D—(pCl)Phe$^1$, D—(pCl)Phe$^2$, D—Trp$^3$, D—Arg$^6$, D—Arg$^{10}$] LHRH
[Ac—D—Nal(2)$^1$, D—(pCl)Phe$^2$, D—Trp$^3$, D—hArg(Et$_2$)$^6$, D—Arg$^{10}$] LHRH

The foregoing agents can be obtained by synthetic processes and general methods of manufacture which can be derived from those published in J. M. Stewart and J. D. Young, "Solid Phase Peptide Synthesis", W. H. Freeman & Co., San Francisco (1969); E. Schroder and K. Lubke, "The Peptides," Vol. 1, Academic Press, New York (1965); E. Kaiser, et al., "Analyt. Biochemistry" 34,595 (1970); Fujino et al., "Biochem. Biophys. Res. Comm., 57, 1248–1256 (1974); J. A. Vilchez-Martinez et al., "Biochem. Biophys. Res. Comm., 59, 1226–1232 (1974); Merrifield, "J. Am. Chem. Soc.", 85, 2149 (1963); Fujino et al. , "Biochem. Biophys. Res. Comm., 49, 863–869 (1972); A. Arimura et al., "Endocrinology," 95, 1174 (1971); J. P. Greenstein and M. Winitz, "Chemistry of the Amino Acids", John Wiley and Sons, Inc., New York and London, Vol. 2, p.1456 (1961); P. Rivaille et al., "Helv. Chim. Acta," 54, 2772 (1971); M. Bodansky and J. T. Sheehan, "Chem. Ind" (London) 38, 1597 (1966); Y. Hirotsu, "Biochem. Biophys. Res. Commun." 59, 277 (1974); M. Fujino et al., "Biochem. Biophys. Res. Commun." 60, 406 (1974); A. S. Dutta et al., "J. Med. Chem." 21, 1018 (1978); J. J. Nestor et al. U.S. Pat. No. 4,234,571; U.S. Pat. No. 4,024,248; U.S. Pat. No. 4,100,274; R. L. Gendrich et al. U.S. Pat. No. 4,005,063; Geiger R, Konig W, Wissmann H, Geisen K, Enzmann F Biochem Biophys Res Commun 45:767–773 (1971); Matsuo H, Arimura A, Nair RMG, Schally AV Biochem Biophys Res Commun 45:822–827 (1971); Monahan M, Rivier J, Burgus R, Amoss M. Blackwell R, Vale W, Guillemin R C R Acad Sc (Paris) Serie D 273:508–510 (1971); Sievertsson H, Chang, JK, Bogentoft C, Currie BL, Folkers K Biochem Biophys Res Commun 44:1566–1571 (1971).

The preferred pharmaceutical form for administration of the LHRH analogs is the pharmaceutically acceptable salt thereof. As used herein, the term "pharmaceutically acceptable salt" refers to salts that retain the desired biological activity of the parent compound and do not impart any undesired toxicological effects. Examples of such salts include acetates, chlorides, carbonates, sulfides, nitrides, fluorides, hydroxides, oxides, and phosphates.

The compositions of the present invention contain a therapeutically effective amount of an LHRH analog alone or in combination with a therapeutically effective amount of a second LHRH analog.

As stated hereinabove, the LHRH analogs of the present invention may be LHRH agonists or LHRH antagonists. The LHRH analog may be administered alone in a pharmaceutically acceptable carrier or with a second LHRH analog in a pharmaceutically acceptable carrier. According to the present invention, a first LHRH agonist may be administered in combination with a second LHRH agonist; an LHRH agonist may be administered in combination with an LHRH antagonist; or a first LHRH antagonist may be administered in combination with a second LHRH antagonist. According to the present invention, the LHRH analogs may be administered in any combination.

The efficaciousness of treatment may be enhanced by administering compositions of the type combining an LHRH agonist with an LHRH antagonist. Such compositions act to both block the LHRH receptor by a competitive binding mechanism and desensitize the responsiveness of the pituitry to LHRH. According to the present invention, preferred combinations are Nafarelin-Detirelix Leuprolide-Ganirelix, and Histrelin-Gonadorelin. However, as stated above, any LHRH agonist/LHRH antagonist combination is suitable.

As used herein, the term "therapeutically effective amount" is intended to mean an amount of the LHRH analog that provides suppression of testosterone formation sufficient for treating male-pattern baldness. The exact dose and regimen for administration will be dependent upon the needs of the individual subject being treated, the type of treatment and the type of LHRH analogs used. However, the preferred therapeutic amount of the LHRH analog ranges from about 0.50 to 8 percent weight/weight in the composition for all routes and forms of administration.

Once treatment according to the present invention commences, serum concentrations of testosterone, FSH, LH and the LHRH analog should not exceed those shown below:

| | |
|---|---|
| Testosterone | 2–10 nmol/l |
| FSH | 2–10 IU/l |
| LH | 2–10 IU/l |
| LHRH analog | 0.36 ng/ml–2.50 ng/nl |

The tests for determining the foregoing concentrations are tests well known in the art, such as plasma assays for testosterone, LH, and FSH. Plasma testosterone may be measured with an antiserum against a testosterone-3-(0-carboxymethyl) oxime-BSA conjugate raised in rabbits and coupled to microcrystalline cellulose. Testosterone concentrations may be determined with a 125I-radioligand and a solid-phase separation technique (celite column chromatography). LH and FSH may be measured with a double-antibody radioimmunoassay procedure similar to that previously described. LHRH analogs may be measured by non-specific radioimmunoassay methods.

Suitable dosages of the LHRH analogs range from 0.2 mg to 360 mg/month for all methods of administration, except the oral route. For the oral route of administration, dosages must contain 200 to 300 times the foregoing amounts of LHRH analog to obtain suitable concentrations of LHRH analog in the blood plasma. Preferred dosages for certain of the preferred LHRH analogs of the present invention are as follows:

| | |
|---|---|
| Nafarelin Acetate | 200–1600 µg/day |
| | 7.5–15 mg/month |
| Leuprolide Acetate | 7.5–15 mg/month |
| Cetrorelix | 3.6–90 mg/month |
| Goserelin Acetate | 3.6 mg/28 days |
| Buserelin Acetate | 3.6–15 mg/month |
| [D—Trp$^6$] [LHRH] | 3.6–15 mg/month |

The LHRH analogs of this invention are typically administered as pharmaceutical compositions of pharmaceutically acceptable carriers combined with the active agent. As used herein, a pharmaceutically acceptable carrier is one which permits convenient administration of the LHRH analog or analogs without imparting undesirable toxicologic effect. Such pharmaceutically acceptable carriers include benzalkonium chloride, sodium hydroxide, water, gelatin, mannitol, carboxymethyl cellulose, polysorbate, polymers, acetic acid, hydrochloric acid, sorbitol, D, L-lactic and glycolic acids copolymer, benzyl alcohol, butylparaben, castor oil, cellulose, corn starch, edetate calcium disodium, hydroxypropyl methylcellulose, magnesium stearate, propylparaben, sodium lauryl sulfate, sodium citrate, sodium proprionate, sodium starch glycolate, titanium dioxide, colloidal silicon dioxide, stearic acid, polyethylene glycol, glycerin, peppermint oil, saccharin sodium, cellulose acetate, hydroxypropyl cellulose, polyethylene oxide, red ferric oxide, sodium chloride, and others.

In the practice of the method of this invention the compositions containing the LHRH analog or analogs discussed hereinabove, are administered to the patient in need of, or desiring, such treatment. These compositions may be administered by any of a variety of routes, including parenterally, (including subcutaneous, and intramuscular administration), oral, topically, transdermally, transmucosally, or intranasally. The most suitable route in any given case will depend upon the particular analog or analogs used, and the subject involved. The compositions may also be administered by means of slow release, depot or implant formulations as described more fully hereinbelow.

The compositions of this invention may be administered orally as solid tablets, liquid-filled gelatin capsules, or extended release tablets. In the tablet form, the LHRH analog or analogs are mixed with inert ingredients and pressed into tablets. In the liquid-filled gelatin capsule form, the LHRH analog or analogs are dissolved in oil and encapsulated in a gelatin capsule.

The extended release tablets contain therapeutically effective amounts of the LHRH analog or analogs and preferably should dissolve readily after ingestion. Such extended release tablets preferably should release the LHRH analog or analogs within a time period of six to twenty-four hours. Pharmaceutically acceptable carriers for the oral route of administration include corn starch, cellulose, colloidal silicon dioxide, sodium citrate, sodium starch glycolate and stearic acid and combinations thereof.

The compositions of this invention may be administered topically. The topical formulation can be, for example, in the form of a solution, suspension, emulsion, gel, or cream of either the oil-in-water or oil-in-oil type, ointment, paste, jelly, or powder. Suitable pharmaceutically acceptable carriers for topical administration may be of any conventional type such as oleaginous bases, for example, cottonseed oil, petrolatum, white petrolatum, mineral oils, silicones, such as dimethylpolysiloxane, or methylphenylpolysiloxane, lanolins, polyethyleneglycol, glyceryl monosterate, methylcellulose, and hydroxymethylcellulose. The topical formulation may contain pharmaceutically acceptable surfactants, wetting agents, dispersing agents, emulsifiers, penetrants, emollients, preservatives, and coloring agents. In the preferred topical formulation, the LHRH analog or analogs is constituted in a mixture of propylene glycol, glycerin, ethanol, water, and other suitable carriers. The topical formulation is applied to the skin, preferably the skin under the arm pits, thereby avoiding the need to affect the patient's coiffure.

The compositions of this invention may be adapted for transdermal delivery. As used herein, "transdermal delivery" is intended to mean transfer of the active agent or agents, LHRH analog or analogs, from the skin surface into the stratum corneum and its subsequent diffusion through the stratum corneum and underlying epidermis, through the dermis, and into the circulation. Suitable transdermal delivery devices permit effective diffusion and permeation of the LHRH analog or analogs from the transdermal delivery device and onto the skin surface. Such devices may be made of macroporous films and membranes, microporous films or nonporous films and membranes. An example of this delivery system is a multilayered rectangular film containing an LHRH analog or analogs as the active agent:

Occlusive backing
Drug reservoir
Rate-controlling membrane
Contact adhesive
Protective liner
(Skin surface)

The occlusive backing may consist of polyethylene/aluminum/polyester/ethyl-vinyl acetate copolymer. The drug reservoir holding the LHRH analog or analogs may be contained in an ethylene-vinyl acetate copolymer matrix. The rate-controlling membrane consists of polyethylene. The contact adhesive may be a polyisobutylene-based material. The protective liner covering the adhesive may be made of a variety of materials. However, the liner must be removed before application to the skin. Accordingly, the LHRH analog or analogs may be incorporated into a transdermal delivery system and applied to the skin.

The compositions of this invention may be administered transmucosally. For this type of administration, the LHRH analog or analogs is preferably incorporated into a suppository and inserted into the rectum once to twice per day. The preferred suppository base should be nontoxic and nonirritating to mucous membranes and should melt or dissolve in rectal fluids. Alternatively, the LHRH analog or analogs may be dissolved in an oil based solution. The solution is then incorporated into a liquid-filled gelatin capsule. Suitable suppository bases include cocoa butter, glycerinated gelatin, hydrogenated vegetable oils, mixtures of polyethylene glycols of various molecular weights, and fatty acid esters or polyethylene glycol.

The compositions of the present invention may also be administered transmucosally as intranasal forms, including powders, pastes, nasal drops or spray. Formulations for intranasal administration may be solid and contain as excipients, for example, lactose, or may be aqueous or oily solutions for administration in the form of nasal drops. In intranasal paste formulations, the LHRH analog or analogs is incorporated into a paste mixture preferably comprised of petrolatum, D-mannitol, carboxymethylcellulose and polysorbate. A thin layer of the paste is applied over the nasal mucosa one to two times per day. In inhalation administration, the composition containing the LHRH analog or analogs is sprayed into the nasal cavity and inhaled into the lungs two to six times per day. For inhalation administration when calibrated spray pumps are used, the pharmaceutically acceptable carrier preferably comprises benzalkonium chloride, glacial acetic acid, sodium hydroxide, hydrochloric acid, sorbitol, D-mannitol, polysorbate and water. For inhalation administration the LHRH analog composition is packaged into a nasal spray bottle. In such administration the pharmaceutically acceptable carrier preferably comprises water, sodium chloride, D-mannitol, carboxymethylcellulose, and polysorbate. The spray is inhaled through the nostrils after the spray bottle is squeezed. The frequency of administration is two to six times each day.

The compositions of this invention may be administered parenterally by subcutaneous or intramuscular injection. Formulations for parenteral administration may contain as common excipients sterile water or saline, polyalkylene glycols such as polyethylene glycol, oils of vegetable origin, hydrogenated naphthalene and the like. Frequency of administration may vary from a single monthly injection to a single yearly injection.

The LHRH analog or analogs is preferably incorporated into a delayed release depot preparation. For depot administration, the pharmaceutically acceptable carrier preferably comprises water, benzalkonium chloride, sodium hydroxide, gelatin, mannitol, carboxymethylcellulose, polysorbate polymer, acetic acid, sorbitol, and D, L-lactic and glycolic acids copolymer. The LHRH analog or analogs are preferably microencapsulated in the carrier. As used herein, "microencapsulation" is the process by which the LHRH analog is incorporated into a matrix of D, L-lactic and glycolic acids copolymer microspheres. Using a syringe, the microsphere preparation is injected into the fatty area of the abdomen. LHRH agonist and LHRH antagonist combinations are preferably administered as depot formulation because slow release of the active agents is accomplished, thereby maximizing the dual action of competitive antagonism and desensitization of the pituitary.

Alternatively, the compositions of the present invention may be administered by subdermal implants. Suitable implants should hold sufficient quantity of the LHRH analog in its reservoir to provide release of therapeutic effective amounts of the LHRH analog over a period, as short as one year to as long as five years. An example of this subdermal implant system is a flexible closed capsule made of Silastic (a dimethylsilofane/methylvinylsiloxane copolymer) containing the LHRH analog. The implant may be shaped as a capillary tube 2.4×34 mm or as a flat capsule 4×20 mm.

The following examples are illustrative of the invention. However, they should not be construed as limiting the invention in any way. Those skilled in the art will appreciate that variations are possible which are within the scope of the present invention.

EXAMPLE I

Depot Formulation

The LHRH analog is microencapsulated in a mixture containing gelatin, D, L-lactic and glycolic acids copolymer, and D-mannitol. A separate vial containing a sterile solution called the diluent is prepared from carboxymethylcellulose sodium, polysorbate, D-mannitol, and water. Just prior to administration, the microencapsulated LHRH analog is mixed with the diluent. Using a 16 gauge syringe, the solution of microencapsulated LHRH analog is injected into the fatty area of the abdomen. The ingredients and their respective concentrations are as follows:

|  | INGREDIENTS | WEIGHT % |
|---|---|---|
| Microencapsulated Microspheres | Leuprolide Acetate | 3% |
|  | Gelatin | 3% |
|  | D, L-lactic and glycolic acids copolymer | 85% |
|  | D-mannitol | 9% |
| Diluent | Carboxymethyl cellulose sodium | 1% |
|  | Polysorbate | 0.2% |
|  | D-mannitol | 6.8% |
|  | Water | 92% |

EXAMPLE II

Depot Formulation

The LHRH agonist and LHRH antagonist, as in Example I, are microencapsulated in a mixture containing gelatin, D, L-lactic and glycolic acids copolymer, and D-mannitol. A separate vial containing a sterile solution called the diluent is prepared from carboxymethylcellulose sodium, polysorbate, D-mannitol, and water. Just prior to administration, the microencapsulated LHRH agonist and LHRH antagonist are mixed with the diluent. Using a 16 gauge syringe, a solution of the microencapsulated LHRH agonist and LHRH antagonist is injected into the fatty area of the abdomen. The ingredients and respective concentrations are as follows:

|  | INGREDIENTS | WEIGHT % |
|---|---|---|
| Microencapsulated Microspheres | Nafarelin | 3% |
|  | Detirelix | 2% |
|  | Gelatin | 3% |
|  | D, L-lactic and glycolic acids copolymer | 85% |
|  | D-mannitol | 7% |
| Diluent | Carboxymethylcellulose sodium | 1% |
|  | Polysorbate | 0.2% |
|  | D-mannitol | 6.8% |
|  | Water | 92% |

EXAMPLE III

Subdermal Implant Formulation

A one to five year dose of microencapsulated LHRH analog is loaded into the reservoir of the implant. Through a one-eighth inch incision made in any obscured fatty region of the body, a pocket is developed in the fatty tissue. The implant is then inserted into the pocket and the incision is closed by one biodegradable suture. The ingredients and respective concentrations are as follows:

| INGREDIENTS | WEIGHT % |
|---|---|
| Nafarelin Acetate | 4% |
| Gelatin | 3% |
| D, L-lactic and glycolic acids copolymer | 84% |
| D-mannitol | 9% |

EXAMPLE IV

Transmucosal Suppository Formulation

The LHRH analog is incorporated into a solid mixture of water soluble vehicle. The mixture is formed into a suppository shape and coated for ease of insertion. The suppository is inserted into the rectum one to twice per day. The ingredients of the suppository and their respective concentrations are as follows:

| INGREDIENTS | WEIGHT % |
|---|---|
| Cetrorelix | 3% |
| Oil | 89% |
| Gelatin | 4% |
| D-mannitol | 3% |
| Carboxymethyl cellulose | 0.7% |
| Polysorbate | 0.3% |

EXAMPLE V

Intranasal Paste Formulation

The LHRH analog is incorporated into a paste mixture. Using a cotton swab, a thin layer of the paste is applied over the nasal mucosa once each day. The ingredients of the paste mixture and their respective concentrations are as follows:

| INGREDIENTS | WEIGHT % |
|---|---|
| Goserelin Acetate | 6% |
| Petrolatum | 90% |
| D-mannitol | 8% |
| Carboxymethyl cellulose | 0.7% |
| Polysorbate | 0.3% |

EXAMPLE VI

Intranasal Spray Formulation

The LHRH analog is incorporated into a solution described below. The solution is applied from a calibrated spray pump. Each spray contains 50–300 µl of solution. Each spray also contains 50–400 µg of LHRH analogs. The ingredients of the solution and their respective concentrations are as follows:

| INGREDIENTS | WEIGHT % |
|---|---|
| Buserelin Acetate | 6.0% |
| Bezalkonium chloride | 0.2% |
| Glacial acetic acid | 0.2% |
| Sodium hydroxide | 0.2% |
| Hydrochloric acid | 0.2% |
| Sorbitol | 0.3% |
| D-mannitol | 3.0% |
| Polysorbate | 0.3% |
| Water | 89.6% |

EXAMPLE VII

Inhalation formulation

The LHRH analog is incorporated into a solution. The solution is packaged into a nasal spray bottle. The spray is inhaled through the nose after the spray bottle is squeezed. The frequency of administration is two to six times each day. The ingredients and their respective concentrations are as follows:

| INGREDIENTS | WEIGHT % |
|---|---|
| Nafarelin Acetate | 6% |
| Water | 87% |
| NaCl | 3% |
| D-mannitol | 3% |
| Carboxymethyl cellulose | 0.7% |
| Polysorbate | 0.3% |

EXAMPLE VIII

Topical Formulation

The LHRH analog is incorporated into a solution of propylene glycol, glycerine, ethanol, and water. The solution is applied to the skin, preferably to the arm pit area twice each day. The ingredients and their respective concentrations are as follows:

| INGREDIENTS | WEIGHT % |
|---|---|
| [Dtrp6] [LHRH] | 6% |
| Water | 70% |
| Ethanol | 10% |
| Propylene glycol | 10% |
| Glycerine | 4% |

EXAMPLE IX

Transdermal Patch Formulation

The LHRH analog is incorporated into the reservoir of a transdermal skin patch. The patch is applied to the skin. The patch will release therapeutic amount of medicine lasting one to three days. The ingredients and their respective concentrations are as follows:

| INGREDIENTS | WEIGHT % |
|---|---|
| Ramorelix | 6% |
| Ethylene - vinyl acetate copolymer matrix | 94% |

EXAMPLE X

Oral Solid Tablet Formulation

The LHRH analog is incorporated into a mixture of inert ingredients and pressed into tablets. The tablets containing therapeutically effective amounts of LHRH analog lasting six to twenty-four hours, dissolve readily after ingestion. The ingredients and their respective concentrations are as follows:

| INGREDIENTS | WEIGHT % |
|---|---|
| Antide | 5% |
| Corn Starch | 90% |
| Cellulose | 1% |
| Colloidal silicon dioxide | 1% |
| Sodium citrate | 1% |
| Sodium starch glycolate | 1% |
| Stearic acid | 1% |

EXAMPLE XI

Liquid-filled Gelatin Capsule Formulation

The LHRH analog is incorporated and dissolved into an oily liquid which is encapsulated in a gelatin capsule. The capsule containing therapeutic amount of medicine lasting six to twenty-four hours dissolved readily after ingestion. The ingredients and their respective concentrations are as follows:

| INGREDIENTS | WEIGHT % |
|---|---|
| Azaline | 5% |
| Glycerin | 79% |
| Peppermint oil | 1% |
| Polyethylene glycol | 5% |
| Soft gelatin capsule | 5% |
| Water | 5% |

EXAMPLE XII

Oral Extended Release Tablet Formulation

The LHRH analog is incorporated into a mixture of inert ingredients and pressed into the top layer of a two layer tablet system. The top layer, represented by reference number 1 in FIG. 1, is pressed into a bottom layer, represented by reference number 2 in FIG. 1, which is a water activated expanding layer, to form into a tablet shape. The tablet is then coated with water insoluble semipermeable membrane, represented by reference number 3 in FIG. 1, which permits water to diffuse through the coating. A small hole or opening (0.4 mm in diameter) represented by reference number 4 in FIG. 1 is drilled through the semi-permeable membrane on the top layer of the tablet. After ingestion, water permeates through the membrane to cause the top layer to dissolve. The water also causes the bottom layer, containing the ingredients and which expands slowly upon contact with water to push the dissolved ingredients of the top layer through the small hole drilled through the membrane. This system is designed to deliver active agent at an approximate rate over 24 hours. The system is illustrated in the cross-sectional view shown in FIG. 1. The ingredients and their respective concentrations are as follows:

|  | INGREDIENTS | WEIGHT % |
|---|---|---|
| Top layer | Leuprolide Acetate | 1% |
|  | Polyethylene glycol | 99% |
| Bottom layer | Hydroxypropyl methyl-cellulose | 40% |
|  | Magnesium stearate | 60% |
| Semipermeable Membrane | Cellulose acetate | 95% |
|  | Hydroxypropyl cellulose | 4% |
|  | Titanium oxide | 1% |

Other types of prolonged-acting oral preparations include (1) coated slow-release beads, (2) tablets with slow-release cores, (3) repeated-action tablets, and (4) tableted mixed-release granules. The coated slow-release beads consist of four groups of pellets, about 1 to 2 mm in diameter. One group consist of uncoated beads, a second group with a coating which resist disintegration for three hours, a third group with a 6-hour coating, and the fourth group with a 9-hour coating.

The invention being thus described, it is evident that the same may be varied in many ways. Such variations are not to be regarded as a departure from the spirit and scope of the invention, and all such modifications are intended to be within the scope of the appended claims.

What is claimed:

1. A composition for the treatment of male-pattern baldness comprising a therapeutically effective amount of a non-steroidal, polypeptide analog of LHRH capable of suppressing testosterone formation in patients in the active phases of male pattern baldness and a pharmaceutically acceptable carrier thereof.

2. The composition of claim 1 wherein the LHRH analog is an LHRH agonist.

3. The composition of claim 1 wherein the LHRH analog is an LHRH antagonist.

4. The composition of claim 2 wherein the LHRH agonist is selected from the group consisting of

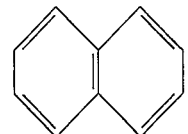

5-oxoPro—His—Trp—Ser—Tyr—N---$\overset{\overset{H}{|}}{\underset{\underset{H}{|}}{C}}$---$\overset{\overset{CH_2}{|}}{C}$—$\overset{\overset{O}{\|}}{}$—Leu—Arg—Pro—

Gly—$NH_2$ 5-oxoPro-His-Trp-Ser-Tyr-D-Leu-Leu-Arg-Pro-$NHC_2H_5$ 5-oxoPro-His-Trp-Ser-Tyr-D-Ser(t-Bu)-Leu-Arg-Pro-$NHNHCONH_2$ 5-oxoPro-His-Trp-Ser-Tyr-D-Ser(t-Bu)-Leu-Arg-Pro-$NHC_2H_5$ 5-oxoPro-His-Trp-Ser-Tyr-$N^t$-benzyl-His-Leu-Arg-Pro-$NHC_2H_5$ 5-oxoPro-His-Trp-Ser-Tyr-Gly-Leu-Arg-Pro-Gly-$NH_2$

[D-Gly(—$CH_2$—S—$Bu^t$)$^6$, Pro$^9$-NHEt] LHRH

[D-Ser($Bu^t$)$^6$, Pro$^9$-NHEt] LHRH

[D-Gly(—$CH_2$—O—$Bu^t$)$^6$, Pro$^9$NHEt] LHRH

[D-Gly(—H)$^6$, Cys($Bu^t$)$^7$, Pro$^9$-NHEt] LHRH

[D-Gly-(—$CH_2$—O—$Bu^t$)$^6$, Cys($Bu^t$)$^7$, Pro$^9$-NHEt] LHRH

[D-Tmo$^6$] LHRH

[D-Trp$^6$, Pro$^9$-NHEt] LHRH

[D-Cha$^6$] LHRH

[D-Pfp$^6$] LHRH

[D-Nal(1)$^6$] LHRH

[D-Nal(2)$^6$] LHRH

[D-Mtf$^6$] LHRH

[D-Ptf$^6$] LHRH

[D-Tmp$^6$] LHRH

[D-Arg$^6$] LHRH

[D-Arg$^6$, Pro$^9$-NHEt] LHRH

[D-hArg$^6$ ($Et_2$)$^6$, Pro$^9$-NHEt] LHRH

[D-Dca$^6$] LHRH

[D-Phe$^6$] LHRH

[D-Ser($Bu^t$)$^6$, Azgly$^{10}$] LHRH

[D-Nal(2)$^6$, aza-Gly$^{10}$] LHRH

[D-Nal(2)$^6$] LHRH

[D-Nal(2)$^6$, Pro$^9$-NHEt] LHRH

[D-Ser($Bu^t$)$^6$, aza-Gly$^{10}$] LHRH

[D-Trp$^6$] LHRH

[D-Trp$^6$, Pro$^9$-NHEt] LHRH

[D-His(Bzl)$_6$, Pro$^9$-NHEt] LHRH and

[D-Nal(2)$^6$, aza-Gly$^{10}$] LHRH.

5. The composition of claim 3 wherein the LHRH antagonist is selected from the group consisting of $N^G$, $N^{G'}$-dialkyl-D-homoarginines

[N-Ac-D-Nal(2)$^1$, D-pCl-Phe$^2$, D-Trp$^3$, D-hArg($Et_2$)$^6$, D-Ala$^{10}$] LHRH

[N-Ac-D-Nal(2)$^1$, D-pClPhe$^2$, D-Pal(3)$^3$, D-hArg($Et_2$)$^6$, L-hArg($Et_2$)$^8$, D-Ala$^{10}$] LHRH,

[Ac-D-Nal(2)-D-pCl-phe-D-Trp-Ser-Tyr-D-Ser(Rha)-Leu-Arg-Pro-AzGly-$NH_2$] LHRH, (Ac-D-Nal(2)$^1$, D-Phe(4Cl)$^2$, D-Pal(3)$^3$, D-Cit$^6$, D-Ala$^{10}$) LHRH, Nal-Glu (Ac-D-Nal(2)1, D-Phe(4Cl)2, D-Pal 3, Arg5, D-Glu⁶ (AA), D-Ala¹⁰)

(Ac-D-Nal(2)¹, D-pCl-Phe², D-Trp³, D-hArg(Et₂)⁶, D-Ala¹⁰), (Ac-Δ3Prol, 4F-D-Phe2, D-Trp3, 6)

(Ac-DNal-DCpa-DPal-Ser-Arg-D-2-amino-5-oxo-5-(4-methoxyphenol) pentanoic acid-Leu-Arg-Pro-DAla-NH₂),

[Ac-DNal¹, DCpa², Dpal³, Lys⁵(Atz), DLys⁶ (Atz), ILys⁸, DAla¹⁰] LHRH,

[Ac-DNal¹, DCpa², DPal³, Aph⁵(Atz), DAph⁶(Atz), ELys⁸, DAla¹⁰]-LHRH,

[N-Ac-D-2-Nal¹, DpClphe², D-3-Pal³, NicLys⁵, D-NicLys⁶, ILys⁸, D-Ala¹⁰] LHRH,

[N-Ac-D-2-Nal¹, D-Phe², D-3-Pal³, NicLys⁵, D-NicLys⁶, ILys⁸, D-Ala¹⁰] LHRH

[N-Ac-D-Nal(2)¹, D-pF-Phe², D-Trp³, D-Arg⁶] GnRH

[N-Ac-D-Nal(2)¹, D-pCl-Phe², D-Pal(3)³, Arg⁵, D-Glu(AA)⁶, D-Ala¹⁰] GnRH

[N-Ac-D-Nal(2)¹, D-pCl-Phe², D-Trp³, D-hArg(Et)₂⁶, D-Ala¹⁰] GnRH

[N-Ac-D-Nal(2)¹, D-pCl-Phe², D-Pal(3)³, D-hArg(Et)₂⁶, Phe⁷, D-Ala¹⁰] GnRH

[N-Ac-D-Nal(2)¹, D-pCl-Phe², D-Trp³, D-hArg(CH₂)₃⁶, D-Ala¹⁰] GnRH

[N-Ac-D-Nal(2)¹, D-pCl-Phe², D-Pal(3)³,⁶, Arg⁵, hArg(Et₂)⁸, D-Ala¹⁰] GnRH

[N-Ac-D-Nal(2)¹, D-pCl-Phe², D-Pal(3)³,⁶, Arg⁵, hArg(CH₂)₃⁸, D-Ala¹⁰] GnRH

[N-Ac-D-Nal(2)¹, D-pF-Phe², D-Pal(3)³,⁶, Arg⁵, hArg(CH²)₃⁸, D-Ala¹⁰] GnRH

[N-Ac-D-Nal(2)¹, D-pCl-Phe², D-Pal(3)³,⁶, Arg⁵, hArg(CH₂CF₃)₂⁸, D-Ala¹⁰] GnRH

[N-Ac-D-Nal(2)¹, D-pCl-Phe², D-Trp³,⁶, Arg⁵, hArg(CH₂)₃⁸, D-Ala¹⁰] GnRH

[N-Ac-D-Nal(2)¹, D-pCl-Phe², D-Trp³,⁶, Arg⁵, hArg(CH₂CF₃)₂⁸, D-Ala¹⁰] GnRH

[N-Ac-D-Nal(2)¹, D-pF-Phe², D-Pal(3)³,⁶, hArg(Et)₂⁵,⁸, D-Ala¹⁰] GnRH

[N-Ac-D-Nal(2)¹, D-pCl-Phe², D-Pal(3)³,⁶, hArg(Bu)⁵,⁸, D-Ala¹⁰] GnRH

[N-Ac-D-Nal(2)¹, D-pCl-Phe², D-Pal(3)³, D-Tyr⁶, hArg(CH₂CF₃)₂⁵,⁸, D-Ala¹⁰] GnRH

[N-Ac-D-Nal(2)¹, D-pCl-Phe², D-pal(3)³,⁶, hArg(Et)₂⁸, D-Ala¹⁰] GnRH

[N-Ac-D-Nal(2)¹, D-pCl-Phe², D-Pal(3)³,⁶, hArg(CH₂)₃⁸, D-Ala-¹⁰] GnRH

[N-Ac-D-Nal(2)¹, D-pCl-Phe², D-Pal(3)³,⁶, hArg(Bu)⁸, D-Ala¹⁰] GnRH

[N-Ac-D-Nal(2)¹, D-pCl-Phe², D-Pal(3)³,⁶ Pal(3)⁵, hArg(CH₂CF₃)₂⁸, D-Ala¹⁰] GnRH

[N-Ac-D-Nal(2)¹, D-pCl-Phe², D-Trp³,⁶, hArg(Et)₂⁸, D-Ala¹⁰] GnRH

[N-Ac-D-Nal(2)¹, D-pCl-Phe², D-Trp³,⁶, hArg(CH₂)₃⁸, D-Ala¹⁰] GnRH

[N-Ac-D-Nal(2)¹, D-pCl-Phe², D-Trp³,⁶, hArg(Bu)⁸, D-Ala¹⁰] GnRH

[N-Ac-D-Nal(2)¹, D-pCl-Phe², D-Trp³,⁶, hArg(CH₂CF₃)₂⁸, D-Ala¹⁰] GnRH

[N-Ac-D-Nal(2)¹, D-pCl-Phe², D-Pal(3)³, D-hArg(Et)₂⁶, hArg(Et₂)⁸, D-Ala¹⁰] GnRH

[N-Ac-D-Nal(2)¹, D-pCl-Phe², D-Pal(3)³, D-hArg(CH₂)₃⁶, hArg(CH₂)₃⁸, D-Ala¹⁰] GnRH

[N-Ac-D-Nal(2)¹, D-pCl-Phe², D-Pal(3)³, D-hArg(Bu)⁶, hArg(Bu)₁⁸, D-Ala¹⁰] GnRH

[N-Ac-D-Nal(2)¹, D-pF-Phe², D-Pal(3)³, D-hArg(ET)₂⁶, hArg(Et)₂⁸, D-Ala¹⁰] GnRH

[N-Ac-D-Nal(2)¹, D-pF-Phe², D-Pal(3)³, D-hArg(Bu)⁶, hArg(CH₂CF₃)₂⁸, D-Ala¹⁰] GnRH

[N-Ac-D-Nal(2)¹, D-pF-Phe², D-Pal(3)³, D-hArg(CH₂CF₃)₂⁶, hArg(Et)₂⁸, D-Ala¹⁰] GnRH

[N-Ac-D-Nal(2)¹, D-pCl-Phe², D-Trp³, D-hArg(Et)₂⁶, hArg(Et)₂⁸, D-Ala¹⁰] GnRH

[N-Ac-D-Nal(2)¹, D-pCl-Phe², D-Trp³, D-hArg(CH₂)₃⁶, hArg(CH₂)₃⁸, D-Ala¹⁰] GnRH

Ac-D-Na(2) D-Phe-(4Cl) D-Pal(3) Ser Tyr D-Lys(A₂pr(Ac)₂) Leu Arg Pro D-Ala-NH₂

Ac-D-Na(2) D-Phe-(4Cl) D-Pal(3) Ser Tyr D-Lys(A₂pr(For)₂) Leu Arg Pro D-Ala-NH

Ac-D-Na(2) D-Phe-(4Cl) D-Pal(3) Ser Tyr D-Lys(A₂bu(For)₂) Leu Arg Pro D-Ala-NH₂

Ac-D-Na(2) D-Phe-(4Cl) D-Pal(3) Ser Tyr D-Lys(A₂bu(Prl)₂) Leu Arg Pro D-Ala-NH

Ac-D-Na(2) D-Phe-(4Cl) D-Trp Ser Arg D-Lys(A₂pr(For)₂) Leu Arg Pro D-Ala-NH

Ac-D-Na(2) D-Phe-(4Cl) D-Pal(3) Ser Tyr D-Lys(A₂pr(EtCar)₂) Leu Arg Pro D-Ala-NH

Ac-D-Na(2) D-Phe-(4Cl) D-Pal(3) Ser Tyr D-Lys(A₂pr(CHC)₂) Leu Arg Pro D-Ala-NH

Ac-D-Na(2) D-Phe-(4Cl) D-Pal(3) Ser Tyr D-Lys(A₂bu(Car)₂) Leu Arg Pro D-Ala-NH

Ac-D-Na(2) D-Phe-(4Cl) D-Pal(3) Ser Tyr D-Lys(A₂pr(BZ)₂) Leu Arg Pro D-Ala-NH

Ac-D-Na(2) D-Phe-(4Cl) D-Pal(3) Ser Tyr D-Lys(A₂bu(Ac)₂) Leu Arg Pro D-Ala-NH

Ac-D-Na(2) D-Phe-(4Cl) D-Pal(3) Ser Tyr D-Lys (A₂bu(CHC)₂) Leu Arg Pro D-Ala-NH

Ac-D-Na(2) D-Phe-(4Cl) D-Pal(3) Ser Tyr D-Lys(A₂bu(LAU)₂) Leu Arg Pro D-Ala-NH

Ac-D-Na(2) D-Phe-(4Cl) D-Pal(3) Ser Tyr D-Lys(A₂pr(Car)₂) Leu Arg Pro D-Ala-NH

[N-Ac-D-Phe¹, D-pCl-Phe², D-Trp³, D-Arg⁶, D-Ala¹⁰] LHRH

[N-Ac-D-Nal(2)¹, D-pF-Phe², D-Trp³, D-Arg⁶]LHRH

[N-Ac-D-pCl-Phe¹, D-pCl-Phe², D-Trp³, D-hArg(Me₂)⁶, D-Ala¹⁰]LHRH

[N-Ac-D-Nal(2)¹, D-pF-Phe², D-TrP³, D-hArg(Me₂)⁶] LHRH

[N-Ac-D-pCl-Phe¹, D-pCl-Phe², D-Trp³, D-hArg(Et₂)⁶, D-Ala¹⁰]LHRH

[N-Ac-D-pCl-Phe¹, D-pCl-Phe², D-Trp³, D-hArg(Et₂)⁶] LHRH

[N-Ac-D-Nal(2)¹, D-pF-Phe², D-Trp³, D-hArg(Et₂)⁶] LHRH

[N-Ac-D-Nal(2)¹, D-pCl-Phe², D-TrP³, D-hArg(Et₂)⁶] LHRH

[N-Ac-D-Nal(2)¹, D-pCl-Phe², D-Trp³, D-hArg(Et₂)⁶, D-Ala¹⁰]LHRH

[N-Ac-D-pCl-Phe¹, D-pCl-Phe², D-Trp³, D-hArg(Pr₂)⁶, D-Ala¹⁰]LHRH

[N-Ac-D-pCl-Phe¹, D-pCl-Phe², D-Trp³, D-hArg(Pr₂)⁶] LHRH

[N-Ac-D-Nal(2)¹, D-pF-Phe², D-Trp³, D-hArg(Pr₂)⁶]LHRH

[D-Phe²] LHRH

[D-Phe²,⁶] LHRH

[Ac-Pro¹, D-Phe², D-Trp⁶] LHRH

[Ac-D-Phe¹, D-(pCl)Phe², D-Trp³,⁶] LHRH

[Ac-Δ³Pro¹, D-(pF)Phe², D-Trp³,⁶] LHRH

[Ac-D-(pCl)Phe¹, D-(pCl)Phe², D-Trp³, D-Arg⁶, D-Arg¹⁰] LHRH and

[Ac-D-Nal(2)¹, D-(pCl)Phe², D-Trp³, D-hArg(Et₂)⁶, D-Arg¹⁰] LHRH.

6. The composition of claim 1 wherein the therapeutic effective amount of the LHRH analog is sufficient to maintain blood serum concentrations of testosterone at about 2 to 10 nmol/l, FSH at about 2 to 10 IU/l, and LH at about 2 to 10 IU/l.

7. A composition for the treatment of male pattern baldness comprising a therapeutically effective amount of a first non-steroidal, polypeptide analog of LHRH capable of suppressing testosterone formation in patients in the active phases of male pattern baldness, a therapeutically effective amount of a second non-steroidal, polypeptide analog of LHRH capable of suppressing testosterone formation in patients in the active phases of male pattern baldness, and a pharmaceutically acceptable carrier thereof.

8. The composition according to claim 7 wherein the first LHRH analog is an LHRH agonist and the second LHRH analog is an LHRH agonist.

9. The composition according to claim 7 wherein the first LHRH analog is an antagonist and the second LHRH analog is an LHRH antagonist.

10. The composition according to claim 7 wherein the first LHRH analog is an LHRH agonist and the second LHRH analog is an LHRH antagonist.

11. The composition according to claim 8 wherein the first and second LHRH agonists are selected from the group consisting of

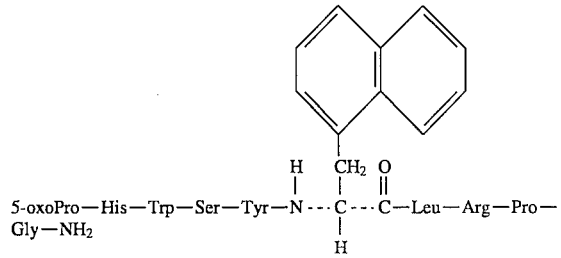

5-oxoPro-His-Trp-Ser-Tyr-D-Leu-Leu-Arg-Pro-NHC₂H₅

5-oxoPro-His-Trp-Ser-Tyr-D-Ser(t-Bu)-Leu-Arg-Pro-NHNHCONH₂

5-oxoPro-His-Trp-Ser-Tyr-D-Ser(t-Bu)-Leu-Arg-Pro-NHC₂H₅

5-oxoPro-His-Trp-Ser-Tyr-N$^τ$-benzyl-His-Leu-Arg-Pro-NHC₂H₅

5-oxoPro-His-Trp-Ser-Tyr-Gly-Leu-Arg-Pro-Gly-NH₂

[D-Gly(—CH₂—S—Bu$^t$)⁶, Pro⁹-NHEt] LHRH

[D-Ser(Bu$^t$)⁶, Pro⁹-NHEt] LHRH

[D-Gly(—CH₂—O—Bu$^t$)⁶, Pro⁹-NHEt] LHRH

[D-Gly(—H)⁶, Cys(Bu$^t$)⁷, Pro⁹-NHEt] LHRH

[D-Gly-(—CH₂—O—Bu$^t$)⁶, Cys(Bu$^t$)⁷, Pro⁹-NHEt] LHRH

[D-Tmo⁶] LHRH

[D-Trp⁶, Pro⁹-NHEt] LHRH

[D-Cha⁶] LHRH

[D-Pfp⁶] LHRH

[D-Nal(1)⁶] LHRH

[D-Nal(2)⁶] LHRH

[D-Mtf⁶] LHRH

[D-Ptf⁶] LHRH

[D-Tmp⁶] LHRH

[D-Arg⁶] LHRH

[D-Arg⁶, Pro⁹-NHEt] LHRH

[D-hArg⁶ (Et₂)⁶, Pro⁹-NHEt] LHRH

[D-Dca⁶] LHRH

[D-Phe⁶] LHRH

[D-Ser(Bu$^t$)⁶, Azgly¹⁰] LHRH

[D-Nal(2)⁶, aza-Gly¹⁰] LHRH

[D-Nal(2)⁶] LHRH

[D-Nal(2)⁶, Pro⁹-NHEt] LHRH

[D-Ser(Bu$^t$)⁶, aza-Gly¹⁰] LHRH

[D-Trp⁶] LHRH

[D-Trp⁶, Pro⁹-NHEt] LHRH

[D-His(Bzl)⁶, Pro⁹-NHEt] LHRH and

[D-Nal(2)⁶, aza-Gly¹⁰] LHRH.

12. The composition according to claim 9 wherein the first and second LHRH antagonist are selected from the group consisting of N$^G$, N$^{G'}$-dialkyl-D-homoarginines

[N-Ac-D-Nal(2)¹, D-pCl-Phe², D-Trp³, D-hArg(Et₂)⁶, D-Ala¹⁰] LHRH

[N-Ac-D-Nal(2)¹, D-pClPhe², D-pal(3)³, D-hArg(Et₂)⁶, L-hArg(Et₂)⁸, D-Ala¹⁰] LHRH,

[Ac-D-Nal(2)-D-pCl-Phe-D-TrP-Ser-Tyr-D-Ser(Rha)Leu-Arg-Pro-AzGly-NH₂] LHRH, (Ac-D-Nal(2)¹, D-Phe(4Cl)², D-Pal(3)³, D-Cit⁶, D-Ala¹⁰) LHRH,

Nal-Glu(Ac-D-Nal(2)1, D-Phe(4Cl)2, D-Pal 3, Arg5, D-Glu⁶ (AA), D-Ala¹⁰)

(Ac-D-Nal(2)¹, D-pCl-Phe², D-Trp³, D-hArg(Et2)⁶, D-Ala¹⁰), (Ac-Δ3Pro1, 4F-D-Phe2, D-Trp3, 6)

(Ac-DNal-DCpa-DPal-Ser-Arg-D-2-amino-5-oxo-5-(4-methoxyphenol) pentanoic acid-Leu-Arg-Pro-DAla-NH₂),

[Ac-DNal¹, DCpa², Dpal³, Lys⁵(Atz), DLys⁶ (Atz), ILys⁸, DAla¹⁰] LHRH,

[Ac-DNal¹, DCpa², DPal³, APh⁵(Atz), DAph⁶(Atz), ELys⁸, DAla¹⁰]-LHRH,

[N-Ac-D-2-Nal¹, DpClPhe², D-3-Pal³, NicLys⁵, D-NicLys⁶, ILys⁸, D-Ala¹⁰] LHRH,

[N-Ac-D-2-Nal¹, D-Phe², D-3-Pal³, NicLys⁵, D-NicLys⁶, ILys⁸, D-Ala¹⁰] LHRH

[N-Ac-D-Nal(2)¹, D-pF-Phe², D-Trp³, D-Arg⁶] GnRH

[N-Ac-D-Nal(2)¹, D-pCl-Phe², D-Pal(3)³, Arg⁵, D-Glu(AA)⁶, D-Ala¹⁰] GnRH

[N-Ac-D-Nal(2)¹, D-pCl-Phe², D-Trp³, D-hArg(Et)₂⁶, D-Ala¹⁰] GnRH

[N-Ac-D-Nal(2)¹, D-pCl-Phe², D-Pal(3)³, D-hArg(Et)₂⁶, Phe⁷, D-Ala¹⁰] GnRH

[N-Ac-D-Nal(2)¹, D-pCl-Phe², D-Trp³, D-hArg(CH₂)₃⁶, D-Ala¹⁰] GnRH

[N-Ac-D-Nal(2)¹, D-pCl-Phe², D-Pal(3)³,⁶, Arg⁵, hArg(Et₂)⁸, D-Ala¹⁰] GnRH

[N-Ac-D-Nal(2)¹, D-pCl-Phe², D-Pal(3)³,⁶, Arg⁵, hArg(CH₂)₃⁸, D-Ala¹⁰] GnRH

[N-Ac-D-Nal(2)¹, D-pF-Phe², D-Pal(3)³,⁶, Arg⁵, hArg(CH₂)₃⁸, D-Ala¹⁰] GnRH

[N-Ac-D-Nal(2)¹, D-pCl-Phe², D-Pal(3)³,⁶, Arg⁵, hArg(CH₂CF₃)₂⁸, D-Ala¹⁰] GnRH

[N-Ac-D-Nal(2)¹, D-pCl-Phe², D-Trp³,⁶, Arg⁵, hArg(CH₂)₃⁸, D-Ala¹⁰] GnRH

[N-Ac-D-Nal(2)¹, D-pCl -Phe², D-Trp³,⁶, Arg⁵, hArg(CH₂CF₃)₂⁸, D-Ala¹⁰] GnRH

[N-Ac-D-Nal(2)¹, D-pF-Phe², D-Pal(3)³,⁶, hArg(Et)₂⁵,⁸, D-Ala¹⁰] GnRH

[N-Ac-D-Nal(2)¹, D-pCl-Phe², D-Pal(3)³,⁶, hArg(Bu)⁵,⁸, D-Ala¹⁰] GnRH

[N-Ac-D-Nal(2)¹, D-pCl-Phe², D-Pal(3)³, D-Tyr⁶, hArg(CH₂CF₃)₂⁵,⁸, D-Ala¹⁰] GnRH

[N-Ac-D-Nal(2)¹, D-pCl-Phe², D-Pal(3)³,⁶, hArg(Et)₂⁵,⁸, D-Ala¹⁰] GnRH

[N-Ac-D-Nal(2)¹, D-pCl-Phe², D-Pal(3)³,⁶, hArg(CH₂)₃⁸, D-Ala¹⁰] GnRH

[N-Ac-D-Nal(2)¹, D-pCl-Phe², D-Pal(3)³,⁶, hArg(Bu)⁸, D-Ala¹⁰] GnRH

[N-Ac-D-Nal(2)¹, D-pCl-Phe², D-Pal(3)³,⁶ Pal(3)⁵, hArg(CH₂CF₃)₂⁸, D-Ala¹⁰] GnRH

[N-Ac-D-Nal(2)¹, D-pCl-Phe², D-Trp³,⁶, hArg(Et)₂⁸, D-Ala¹⁰] GnRH

[N-Ac-D-Nal(2)¹, D-pCl-Phe², D-Trp³,⁶, hArg(CH₂)₃⁸, D-Ala¹⁰] GnRH

[N-Ac-D-Nal(2)¹, D-pCl-Phe², D-Trp³,⁶, hArg(Bu)⁸, D-Ala¹⁰] GnRH

[N-Ac-D-Nal(2)¹, D-pCl-Phe², D-Trp³,⁶, hArg(CH₂CF₃)₂⁸, D-Ala¹⁰] GnRH

[N-Ac-D-Nal(2)¹, D-pCl-Phe², D-Pal(3)³, D-hArg(Et)₂⁶, hArg(Et)₂⁸, D-Ala¹⁰] GnRH

[N-Ac-D-Nal(2)¹, D-pCl Phe², D-Pal(3)³, D-hArg(CH₂)₃⁶, hArg(CH₂)₃⁸, D-Ala¹⁰] GnRH

[N-Ac-D-Nal(2)¹, D-pCl-Phe², D-Pal(3)³, D-hArg(Bu)⁶, hArg(Bu)₁⁸, D-Ala¹⁰] GnRH

[N-Ac-D-Nal(2)¹, D-pF-Phe², D-Pal(3)³, D-hArg(Et)₂⁶, hArg(Et)₂⁸, D-Ala¹⁰] GnRH

[N-Ac-D-Nal(2)¹, D-pF-Phe², D-Pal(3)³, D-hArg(Bu)⁶, hArg(CH₂CF₃)₂⁸, D-Ala¹⁰] GnRH

[N-Ac-D-Nal(2)¹, D-pF-Phe², D-Pal (3)³, D-hArg(CH₂CF₃)₂⁶, hArg(Et)₂⁸, D-Ala¹⁰] GnRH

[N-Ac-D-Nal(2)¹, D-pCl-Phe², D-Trp³, D-hArg(Et)₂⁶, hArg(Et)₂⁸, D-Ala¹⁰] GnRH

[N-Ac-D-Nal(2)¹, D-pCl-Phe², D-Trp³, D-hArg(CH₂)₃⁶, hArg(CH₂)₃⁸, D-Ala¹⁰] GnRH

Ac-D-Na(2) D-Phe-(4Cl) D-Pal(3) Ser Tyr D-Lys(A₂pr(Ac)₂) Leu Arg Pro D-Ala-NH₂

Ac-D-Na(2) D-Phe-(4Cl) D-Pal(3) Ser Tyr D-Lys (A₂pr(For)₂) Leu Arg Pro D-Ala-NH

Ac-D-Na(2) D-Phe-(4Cl) D-Pal (3) Ser Tyr D-Lys(A₂bu(For)₂) Leu Arg Pro D-Ala-NH₂

Ac-D-Na(2) D-Phe-(4Cl) D-Pal(3) Ser Tyr D-Lys(A₂bu(Prl)₂) Leu Arg Pro D-Ala-NH

Ac-D-Na(2) D-Phe-(4Cl) D-Pal(3) Ser Arg D-Lys (A₂pr(For)₂) Leu Arg Pro D-Ala-NH

Ac-D-Na(2) D-Phe-(4Cl) D-Pal(3) Ser Tyr D-Lys(A₂pr(EtCar)₂) Leu Arg Pro D-Ala-NH

Ac-D-Na(2) D-Phe-(4Cl) D-Pal(3) Ser Tyr D-Lys(A₂pr(CHC)₂) Leu Arg Pro D-Ala-NH

Ac-D-Na(2) D-Phe-(4Cl) D-Pal(3) Ser Tyr D-Lys(A₂bu(Car)₂) Leu Arg Pro D-Ala-NH

Ac-D-Na(2) D-Phe-(4Cl) D-Pal(3) Ser Tyr D-Lys(A₂pr(BZ)₂) Leu Arg Pro D-Ala-NH

Ac-D-Na(2) D-Phe-(4Cl) D-Pal(3) Ser Tyr D-Lys(A₂bu(Ac)₂) Leu Arg Pro D-Ala-NH

Ac-D-Na(2) D-Phe-(4Cl) D-Pal(3) Ser Tyr D-Lys (A₂bu(CHC)₂) Leu Arg Pro D-Ala-NH

Ac-D-Na(2) D-Phe-(4Cl) D-Pal(3) Ser Tyr D-Lys(A₂bu(LAU)₂) Leu Arg Pro D-Ala-NH

Ac-D-Na(2) D-Phe-(4Cl) D-Pal(3) Ser Tyr D-Lys (A₂pr(Car)₂) Leu Arg Pro D-Ala-NH

[N-Ac-D-pCl-Phe¹, D-pCl-Phe², D-Trp³, D-Arg⁶, D-Ala¹⁰]LHRH

[N-Ac-D-Nal(2)¹, D-pF-Phe², D-Trp³, D-Arg⁶]LHRH

[N-Ac-D-pCl-Phe¹, D-pCl-Phe², D-Trp³, D-hArg(Me₂)⁶, D-Ala¹⁰]LHRH

[N-Ac-D-Nal(2)¹, D-pF-Phe², D-Trp³, D-hArg(Me₂)⁶] LHRH

[N-Ac-D-pCl-Phe¹, D-pCl-Phe², D-Trp³, D-hArg(Et₂)⁶, D-Ala¹⁰]LHRH

[N-Ac-D-pCl-Phe¹, D-pCl-Phe², D-Trp³, D-hArg (Et₂)⁶] LHRH

[N-Ac-D-Nal(2)¹, D-pF-Phe², D-Trp³, D-hArg(Et₂)⁶] LHRH

[N-Ac-D-Nal(2)¹, D-pCl-Phe², D-Trp³, D-hArg(Et₂)₆] LHRH

[N-Ac-D-Nal(2)¹, D-pCl-Phe², D-Trp³, D-hArg(Et₂)⁶, D-Ala¹⁰]LHRH

[N-Ac-D-pCl-Phe¹, D-pCl-Phe², D-Trp³, D-hArg(Pr₂)⁶, D-Ala¹⁰]LHRH

[N-Ac-D-pCl-Phe¹, D-pCl -Phe², D-Trp³, D-hArg(Pr₂)⁶] LHRH

[N-Ac-D-Nal(2)¹, D-pF-Phe², D-Trp³, D-hArg(Pr²)⁶LHRH

[D-Phe²] LHRH

[D-Phe²,⁶] LHRH

[Ac-Pro¹, D-Phe², D-Trp⁶] LHRH

[Ac-D-Phe¹, D-(pCl)Phe², D-Trp³,⁶] LHRH

[Ac-Δ³Pro¹, D-(pF)Phe², D-Trp³,⁶] LHRH

[Ac-D-(pCl)Phe¹, D-(pCl)Phe², D-Trp³, D-Arg⁶, D-Arg¹⁰] LHRH and

[Ac-D-Nal(b 2)¹, D-(pCl)Phe², D-Trp³, D-hArg(Et₂)⁶, D-Arg¹⁰] LHRH.

13. The composition according to claim 10 wherein the LHRH agonist is selected from the group consisting of

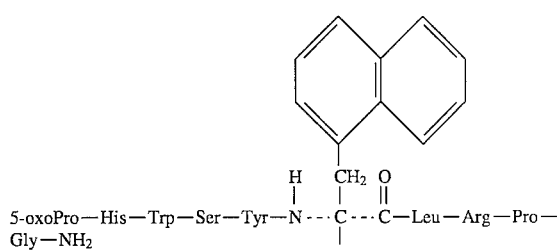

5-oxoPro—His—Trp—Ser—Tyr—N---C---C—Leu—Arg—Pro—Gly—NH₂

5-oxoPro-His-Trp-Ser-Tyr-D-Leu-Leu-Arg-Pro-NHC₂H₅

5-oxoPro-His-Trp-Ser-Tyr-D-Ser(t-Bu)-Leu-Arg-Pro-NHNHCONH₂

5-oxoPro-His-Trp-Ser-Tyr-D-Ser(t-Bu)-Leu-Arg-Pro-NHC₂H₅

5-oxoPro-His-Trp-Ser-Tyr-N$^t$-benzyl-His-Leu-Arg-Pro-NHC$_2$H$_5$ 5-oxoPro-His-Trp-Ser-Tyr-Gly-Leu-Arg-Pro-Gly-NH$_2$

[D-Gly(—CH$_2$—S—Bu$^t$)$^6$, Pro$^9$-NHEt] LHRH

[D-Ser(Bu$^t$)$^6$, Pro$^9$-NHEt] LHRH

[D-Gly(—CH$_2$—O—Bu$^t$)$^6$, Pro$^9$-NHEt] LHRH

[D-Gly(—H)$^6$, Cys (Bu$^t$)$^7$, Pro$^9$-NHEt] LHRH

[D-Gly-(—CH$_2$—O—Bu$^t$)$^6$, Cys(Bu$^t$)$^7$, Pro$^9$-NHEt] LHRH

[D-Tmo$^6$] LHRH

[D-Trp$^6$, Pro$^9$-NHEt] LHRH

[D-Cha$^6$] LHRH

[D-Pfp$^6$] LHRH

[D-Nal(1)$^6$] LHRH

[D-Nal(2)$^6$] LHRH

[D-Mtf$^6$] LHRH

[D-Ptf$^6$] LHRH

[D-Tmp$^6$] LHRH

[D-Arg$^6$] LHRH

[D-Arg$^6$, Pro$^9$-NHEt] LHRH

[D-hArg$^6$ (Et$_2$)$^6$, Pro$^9$-NHEt] LHRH

[D-Dca$^6$] LHRH

[D-Phe$^6$] LHRH

[D-Ser(Bu$^t$)$^6$, Azgly$^{10}$] LHRH

[D-Nal(2)$^6$, aza-Gly$^{10}$] LHRH

[D-Nal(2)$^6$] LHRH

[D-Nal(2)$^6$, Pro$^9$-NHEt] LHRH

[D-Ser(Bu$^t$)$^6$, aza-Gly$^{10}$] LHRH

[D-Trp$^6$] LHRH

[D-Trp$^6$, Pro$^9$-NHEt] LHRH

[D-His(Bzl)$^6$, Pro$^9$NHEt] LHRH and

[D-Nal(2)$^6$, aza-Gly$^{10}$] LHRH and the LHRH antagonist is selected from the group consisting of N$^G$, N$^{G'}$-dialkyl-D-homoarginines

[N-Ac-D-Nal(2)$^1$, D-pCl-Phe$^2$, D-Trp$^3$, D-hArg(Et$_2$)$^6$, D-Ala$^{10}$] LHRH

[N-Ac-D-Nal(2)$^1$, D-pClPhe$^2$, D-Pal(3)$^3$, D-hArg(Et$_2$)$^6$, L-hArg(Et$_2$)$^8$, D-Ala$^{10}$] LHRH,

[Ac-D-Nal(2)-D-pCl-Phe-D-TrP-Ser-Tyr-D-Ser(Rha)Leu-Arg-Pro-AzGly-NH$_2$] LHRH, (Ac-D-Nal(2)$^1$, D-Phe(4Cl)$^2$, D-Pal(3)$^3$, D-Cit$^6$, D-Ala$^{10}$) LHRH,

Nal-Glu (Ac-D-Nal(2)1, D-Phe(4Cl)2, D-Pal 3, Arg5, D-Glu$^6$ (AA), D-Ala$^{10}$), (Ac-D-Nal(2)$^1$, D-pCl-Phe$^2$, D-Trp$^3$, D-hArg(Et2)$^6$, D-Ala$^{10}$)

(Ac-Δ3Prol, 4F-D-Phe2, D-Trp3, 6)

(Ac-DNal-DCpa-DPal-Ser-Arg-D-2-amino-5-oxo-5-(4-methoxyphenol) pentanoic acid-Leu-Arg-Pro-DAla-NH$_2$),

[Ac-DNal$^1$, DCpa$^2$, Dpal$^3$, Lys$^5$(Atz), DLys$^6$ (Atz), ILys$^8$, DAla$^{10}$] LHRH,

[Ac-DNal$^1$, DCpa$^2$, DPal$^3$, Aph$^5$(Atz), DAph$^6$(Atz), ELys$^8$, DAla$^{10}$]-LHRH,

[N-Ac-D-2-Nal$^1$, DpClPhe$^2$, D-3-Pal$^3$, NicLys$^5$, D-NicLys$^6$, ILys$^8$, D-Ala$^{10}$] LHRH,

[N-Ac-D-2-Nal$^1$, D-Phe$^2$, D-3-Pal$^3$, NicLys$^5$, D-NicLys$^6$, ILys$^8$, D-Ala$^{10}$] LHRH

[N-Ac-D-Nal(2)$^1$, D-pF-Phe$^2$, D-Trp$^3$, D-Arg$^6$] GnRH

[N-Ac-D-Nal(2)$^1$, D-pCl-Phe$^2$, D-Pal(3)$^3$, Arg$^5$, D-Glu(AA)$^6$, D-Ala$^{10}$] GnRH

[N-Ac-D-Nal(2)$^1$, D-pCl-Phe$^2$, D-Trp$^3$, D-hArg(Et)$_2^6$, D-Ala$^{10}$] GnRH

[N-Ac-D-Nal(2)$^1$ D-pCl-Phe$^2$, D-Pal(3)$^3$, D-hArg(Et)$_2^6$, Phe$^7$, D-Ala$^{10}$] GnRH

[N-Ac-D-Nal(2)$^1$, D-pCl-Phe$^2$, D-Trp$^3$, D-hArg(CH$_2$)$_3^6$, D-Ala$^{10}$] GnRH

[N-Ac-D-Nal(2)$^1$, D-pCl-Phe$^2$, D-Pal(3)$^{3,6}$, Arg$^5$, hArg(Et$_2$)$^8$, D-Ala$^{10}$] GnRH

[N-Ac-D-Nal(2)$^1$, D-pCl-Phe$^2$, D-Pal(3)$^{3,6}$, Arg$^5$, hArg(CH$_2$)$_3^8$, D-Ala$^{10}$] GnRH

[N-Ac-D-Nal(2)$^1$, D-pF-Phe$^2$, D-Pal(3)$^{3,6}$, Arg$^5$, hArg(CH$_2$)$_3^8$, D-Ala$^{10}$] GnRH

[N-Ac-D-Nal(2)$^1$, D-pCl-Phe$^2$, D-Pal(3)$^{3,6}$, Arg$^5$, hArg(CH$_2$CF$_2$)$_2^8$, D-Ala$^{10}$] GnRH

[N-Ac-D-Nal(2)$^1$, D-pCl-Phe$^2$, D-Trp$^{3,6}$, Arg$^5$, hArg(CH$_2$)$_3^8$, D-Ala$^{10}$] GnRh

[N-Ac-D-Nal(2)$^1$, D-pCl-Phe$^2$, D-Trp$^{3,6}$, Arg$^5$, hArg(CH$_2$CF$_3$)$_2^8$, D-Ala$^{10}$] GnRH

[N-Ac-D-Nal(2)$^1$, D-pF-Phe$^2$, D-Pal(3)$^{3,6}$, hArg(Et)$_2^{5,8}$, D-Ala$^{10}$] GnRH

[N-Ac-D-Nal(2)$^1$, D-pCl-Phe$^2$, D-Pal(3)$^{3,6}$, hArg(Bu)$^{5,8}$, D-Ala$^{10}$] GnRH

[N-Ac-D-Nal(2)$^1$, D-pCl-Phe$^2$, D-Pal(3)$^3$, D-Tyr$^6$, hArg(CH$_2$CF$_3$)$_2^{5,8}$, D-Ala$^{10}$] GnRH

[N-Ac-D-Nal(2)$^1$, D-pCl-Phe$^2$, D-Pal(3)$^{3,6}$, hArg(Et)$_2^8$, D-Ala$^{10}$] GnRH

[N-Ac-D-Nal(2)$^1$, D-pCl-Phe$^2$, D-Pal(3)$^{3,6}$, hArg(CH$_2$)$_{3,8}$, D-Ala$^{10}$] GnRH

[N-Ac-D-Nal(2)$^1$, D-pCl-Phe$^2$, D-Pal(3)$^{3,6}$, hArg(Bu)$^8$, D-Ala$^{10}$] GnRH

[N-Ac-D-Nal(2)$^1$, D-pCl-Phe$^2$, D-Pal (3)$^{3,6}$ Pal(3)$^5$, hArg(CH$_2$CF$_3$)$_2^8$, D-Ala$^{10}$] GnRH

[N-Ac-D-Nal(2)$_1$, D-pCl-Phe$^2$, D-Trp$^{3,6}$, hArg(Et)$_2^8$, D-Ala$^{10}$] GnRH

[N-Ac-Nal(2)$^1$, D-pCl-Phe$^2$, D-Trp$^{3,6}$, hArg(CH$_2$)$_3^8$, D-Ala$^{10}$] GnRH

[N-Ac-D-Nal(2)$^1$, D-pCl-Phe$^2$, D-Trp$^{3,6}$, hArg(Bu)$^8$, D-Ala$^{10}$] GnRH

N-Ac-D-Nal(2)$^1$, D-pCl-Phe$^2$, D-Trp$^{3,6}$, hArg(CH$_2$CF$_3$)$_2^8$, D-Ala$^{10}$] GnRH

[N-Ac-D-Nal(2)$^1$, D-pCl-Phe$^2$, D-Pal(3)$^3$, D-hArg(Et)$_2^6$, hArg(Et$_2$)$^8$, D-Ala$^{10}$] GnRH

[N-Ac-D-Nal(2)$^1$, D-pCl-Phe$^2$, D-Pal(3)$^3$, D-hArg(CH$_2$)$_3^6$, hArg(CH$_2$)$_3^8$, D-Ala$^{10}$] GnRH

[N-Ac-D-Nal(2)$^1$, D-pCl-Phe$^2$, D-Pal(3)$^3$, D-hArg(Bu)$_6$, hArg(Bu)$_1^8$, D-Ala$^{10}$] GnRH

[N-Ac-D-Nal(2)$^1$, D-pF-Phe$^2$, D-Pal(3)$^3$, D-hArg(Et)$_2^6$, hArg(Et)$_2^8$, D-Ala$^{10}$] GnRH

[N-Ac-D-Nal(2)$^1$, D-pF-Phe$^2$, D-Pal(3)$^3$, D-hArg(Bu)$^6$, hArg(CH$_2$CF$_3$)$_2^8$, D-Ala$^{10}$] GnRH

[N-Ac-D-Nal(2)$_2^6$, D-pF-Phe$^2$, D-Pal(3)$^3$, D-hArg(CH$_2$CF$_3$)$_2^6$, hArg(Et)$_2^8$, D-Ala$^{10}$] GnRH

[N-Ac-D-Nal(2)$^1$, D-pCl-Phe$^2$, D-Trp$^3$, D-hArg(Et)$_2^6$, hArg(Et)$_2^8$, D-Ala$^{10}$] GnRH

[N-Ac-D-Nal(2)$^1$, D-pCl-Phe$^2$, D-Trp$^3$, D-hArg(CH$_2$)$_3^6$, hArg(CH$_2$)$_3^8$, D-Ala$^{10}$] GnRH

Ac-D-Na(2) D-Phe-(4Cl) D-Pal(3) Ser Tyr D-Lys(A$_2$pr(Ac)$_2$) Leu Arg Pro D-Ala-NH$_2$

Ac-D-Na(2) D-Phe-(4Cl) D-Pal(3) Ser Tyr D-Lys(A$_2$pr(For)$_2$) Leu Arg Pro D-Ala-NH

Ac-D-Na(2) D-Phe-(4Cl) D-Pal(3) Ser Tyr D-Lys(A₂bu(For)₂) Leu Arg Pro D-Ala-NH₂

Ac-D-Na(2) D-Phe-(4Cl) D-Pal(3) Ser Tyr D-Lys(A₂bu(Prl)₂) Leu Arg Pro D-Ala-NH

Ac-D-Na(2) D-Phe-(4Cl) D-Trp Ser Arg D-Lys(A₂pr(For)₂) Leu Arg Pro D-Ala-NH

Ac-D-Na(2) D-Phe-(4Cl) D-Pal(3) Ser Tyr D-Lys(A₂pr(EtCar)₂) Leu Arg Pro D-Ala-NH

Ac-D-Na(2) D-Phe-(4Cl) D-Pal(3) Ser Tyr D-Lys (A₂pr(CHC)₂) Leu Arg Pro D-Ala-NH

Ac-D-Na(2) D-Phe-(4Cl) D-Pal(3) Ser Tyr D-Lys(A₂bu(Car)₂) Leu Arg Pro D-Ala-NH

Ac-D-Na(2) D-Phe-(4Cl) D-Pal(3) Ser Tyr D-Lys(A₂pr(BZ)₂) Leu Arg Pro D-Ala-NH

Ac-D-Na(2) D-Phe-(4Cl) D-Pal(3) Ser Tyr D-Lys (A₂bu(Ac)₂) Leu Arg Pro D-Ala-NH

Ac-D-Na(2) D-Phe-(4Cl) D-Pal(3) Ser Tyr D-Lys (A₂bu(CHC)₂) Leu Arg Pro D-Ala-NH

Ac-D-Na(2) D-Phe-(4Cl) D-Pal(3) Ser Tyr D-Lys (A₂bu(LAU)₂) Leu Arg Pro D-Ala-NH

Ac-D-Na(2) D-Phe-(4Cl) D-Pal(3) Ser Tyr D-Lys (A₂pr(Car)₂) Leu Arg Pro D-Ala-NH

[N-Ac-D-pCl-Phe$^1$, D-pCl-Phe$^2$, D-Trp$^3$, D-Arg$^6$, D-Ala$^{10}$]LHRH

[N-Ac-D-Nal(2)$^1$, D-pF-Phe$^2$, D-Trp$^3$, D-Arg$^6$]LHRH

[N-Ac-D-pCl-Phe$^1$, D-pCl-Phe$^2$, D-Trp$^3$, D-hArg(Me$_2$)$^6$, D-Ala$^{10}$]LHRH

[N-Ac-D-Nal(2)$^1$, D-pF-Phe$^2$, D-Trp$^3$, D-hArg(Me$_2$)$^6$] LHRH

[N-Ac-D-pCl-Phe$^1$, D-pCl-Phe$^2$, D-Trp$^3$, D-hArg(Et$_2$)$^6$, D-Ala$^{10}$]LHRH

[N-Ac-D-pCl-Phe$^1$, D-pCl- Phe$^2$, D-Trp$^3$, D-hArg(Et$_2$)$^6$] LHRH

[N-Ac-D-Nal(2)$^1$, D-pF-Phe$^2$, D-Trp$^3$, D-hArg(Et$_2$)$^6$] LHRH

[N-Ac-D-Nal(2)$^1$, D-pCl-Phe$^2$, D-Trp$^3$, D-hArg(Et$_2$)$^6$] LHRH

[N-Ac-D-Nal(2)$^1$, D-pCl-Phe$^2$, D-Trp$^3$, D-hArg(Et$_2$)$^6$, D-Ala$^{10}$]LHRH

[N-Ac-D-pCl-Phe$^1$, D-pCl-Phe$^2$, D-Trp$^3$, D-hArg(Pr$_2$)$^6$, D-Ala$^{10}$]LHRH

[N-Ac-D-pCl-Phe$^1$, D-pCl-Phe$^2$, D-Trp$^3$, D-hArg(Pr$_2$)$^6$] LHRH

[N-Ac-D-Nal(2)$^1$, D-pF-Phe$^2$, D-Trp$^3$, D-hArg(Pr$_2$)$^6$LHRH

[D-Phe$^{2,6}$] LHRH

[D-Phe$^{2,6}$] LHRH

[Ac-Pro$^1$, D-Phe$^2$, D-Trp$^6$] LHRH

[Ac-D-Phe$^1$, D-(pCl)Phe$^2$, D-Trp$^{3,6}$] LHRH

[Ac-Δ$^3$Pro$^1$, D-(pF)Phe$^2$, D-Trp$^{3,6}$] LHRH

[Ac-D-(pCl)Phe$^1$, D-(pCl)Phe$^2$, D-Trp$^3$, D-Arg$^6$, D-Arg$^{10}$] LHRH and

[Ac-D-Nal(2)$^1$, D-(pCl)Phe$^2$, D-Trp$^3$, D-hArg(Et$_2$)$^6$, D-Arg$^{10}$] LHRH.

14. The composition according to claim 7 wherein the therapeutically effective amount of the first LHRH analog and the therapeutic effective amount of the second LHRH analog are sufficient to maintain blood serum concentrations of testosterone at about 2 to 10 nmol/l, FSH at about 2 to 10 IU/l, and LH at about 2 to 10 IU/l.

15. A method of treatment of male pattern baldness which comprises the administration of a therapeutically effective amount of a non-steroidal, polypeptide analog of LHRH capable of suppressing testosterone formation in a patient in the active phases of male pattern baldness.

16. The method according to claim 15 wherein the LHRH analog is an LHRH agonist.

17. The method according to claim 15 wherein the LHRH analog is an LHRH antagonist.

18. The method according to claim 16 wherein the LHRH agonist is selected from the group consisting of

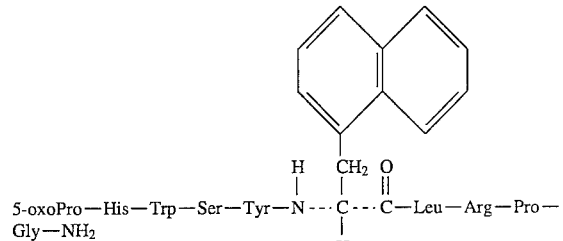

5-oxoPro—His—Trp—Ser—Tyr—N---C---C—Leu—Arg—Pro—Gly—NH₂

5-oxoPro-His-Trp-Ser-Tyr-D-Leu-Leu-Arg-Pro-NHC$_2$H$_5$ 5-oxoPro-His-Trp-Ser-Tyr-D-Ser(t-Bu)-Leu-Arg-Pro-NHNHCONH$_2$ 5-oxoPro-His-Trp-Ser-Tyr-D-Ser(t-Bu)-Leu-Arg-Pro-NHC$_2$H$_5$ 5-oxoPro-His-Trp-Ser-Tyr-N$^t$-benzyl-His-Leu-Arg-Pro-NHC$_2$H$_5$ 5-oxopro-His-Trp-Ser-Tyr-Gly-Leu-Arg-Pro-Gly-NH$_2$

[D-Gly(—CH$_2$—S—Bu$^t$)$^6$, Pro$^9$-NHEt] LHRH

[D-Ser(Bu$^t$)$^6$, Pro$^9$NHEt] LHRH

[D-Gly(—CH$_2$—O—Bu$^t$)$^6$, Pro$^9$-NHEt] LHRH

[D-Gly(—H)$^6$, Cys (Bu$^t$)$^7$, Pro$^9$-NHEt] LHRH

[D-Gly-(—CH$_2$—O—Bu$^t$)$^6$, Cys(Bu$^t$)$^7$, Pro$^9$-NHEt] LHRH

[D-Tmo$^6$] LHRH

[D-Trp$^6$, Pro$^9$-NHEt] LHRH

[D-Cha$^6$] LHRH

[D-Pfp$^6$] LHRH

[D-Nal(1)$^6$] LHRH

[D-Nal(2)$^6$] LHRH

[D-Mtf$^6$] LHRH

[D-Ptf$^6$] LHRH

[D-Tmp$^6$] LHRH

[D-Arg$^6$] LHRH

[D-Arg$^6$, Pro$^9$-NHEt] LHRH

[D-hArg$^6$(Et$_2$)$^6$, Pro$^9$-NHEt] LHRH

[D-Dca$^6$] LHRH

[D-Phe$^6$] LHRH

[D-Ser(Bu$^t$)$^6$, Azgly$^{10}$] LHRH

[D-Nal(2)$^6$, aza-Gly$^{10}$] LHRH

[D-Nal(2)$^6$] LHRH

[D-Nal(2)$^6$, Pro$^9$-NHEt] LHRH

[D-Ser(Bu$^t$)$^6$, aza-Gly$^{10}$] LHRH

[D-Trp$^6$] LHRH

[D-TrP$^6$, Pro$^9$-NHEt] LHRH

[D-His(Bzl)$^6$, Pro$^9$-NHEt] LHRH and

[D-Nal(2)$^6$, aza-Gly$^{10}$] LHRH.

19. The method according to claim 17 wherein the LHRH antagonist is selected from the group consisting of N$^G$, N$^{G'}$-dialkyl-D-homoarginines

[N-Ac-D-Nal(2)$^1$, D-pCl-Phe$^2$, D-Trp$^3$, D-hArg (Et$_2$)$^6$, D-Ala$^{10}$] LHRH

[N-Ac-D-Nal(2)$^1$, D-pClPhe$^2$, D-Pal(3)$^3$, D-hArg(Et$_2$)$^6$, L-hArg(Et$_2$)$^8$, D-Ala$^{10}$] LHRH,

[Ac-D-Nal(2)-D-pCl-Phe-D-Trp-Ser-Tyr-D-Ser(Rha)Leu-Arg-Pro-AzGly-NH$_2$] LHRH, (Ac-D-Nal(2)$^1$, D-Phe(4Cl)$^2$, D-Pal(3)$^3$, D-Cit$^6$, D-Ala$^{10}$) LHRH,

Nal-Glu (Ac-D-Nal(2)1, D-Phe(4Cl)2, D-Pal 3, Arg5, D-Glu$^6$ (AA), D-Ala$^{10}$)

(Ac-D-Nal(2)$^1$, D-pCl-Phe$^2$, D-Trp$^3$, D-hArg(Et2)$^6$, D-Ala$^{10}$), (Ac-Δ3Prol, 4F-D-Phe2, D-Trp3, 6)

(Ac-DNal-DCpa-DPal-Ser-Arg-D-2-amino-5-oxo-5-(4-methoxyphenol) pentanoic acid-Leu-Arg-Pro-DAla-NH$_2$),

[Ac-DNal$^1$, DCpa$^2$, Dpal$^3$, Lys$^5$(Atz), DLys$^6$ (Atz), ILys$^8$, DAla$^{10}$] LHRH,

[Ac-DNal$^1$, DCpa$^2$, DPal$^3$, Aph$^5$(Atz), DAph$^6$(Atz), ELys$^8$, DAla$^{10}$]-LHRH,

[N-Ac-D-2-Nal$^1$, DpClPhe$^2$, D-3-Pal$^3$, NicLys$^5$, D-NicLys$^6$, ILys$^8$, D-Ala$^{10}$] LHRH,

[N-Ac-D-2-Nal$^1$, D-Phe$^2$, D-3-Pal$^3$, NicLys$^5$, D-NicLys$^6$, ILys$^8$, D-Ala$^{10}$] LHRH

[N-Ac-D-Nal(2)$^1$, D-pF-Phe$^2$, D-Trp$^3$, D-Arg$^6$] GnRH

[N-Ac -D-Nal(2)$^1$, D-pCl-Phe$^2$, D-Pal(3)$^3$, Arg$^5$, D-Glu(AA)$^6$, D-Ala$^{10}$] GnRH

[N-Ac-D-Nal(2)$^1$, D-pCl-Phe$^2$, D-Trp$^3$, D-hArg(Et)$_2$$^6$, D-Ala$^{10}$] GnRH

[N-Ac-D-Nal(2)$^1$, D-pCl-Phe$^2$, D-Pal(3)$^3$, D-hArg(Et)$_2$$^6$, Phe$^7$, D-Ala$^{10}$] GnRH

[N-Ac-D-Nal(2)$^1$, D-pCl-Phe$^2$, D-Trp$^3$, D-hArg(CH$_2$)$_3$$^6$, D-Ala$^{10}$] GnRH

[N-Ac-D-Nal(2)$^1$, D-pCl-Phe$^2$, D-Pal(3)$^{3,6}$, Arg$^5$, hArg(Et$_2$)$^8$, D-Ala$^{10}$] GnRH

[N-Ac-D-Nal(2)$^1$, D-pCl-Phe$^2$, D-Pal(3)$^{3,6}$, Arg$^5$, hArg(CH$_2$)$_3$$^8$, D-Ala$^{10}$] GnRH

[N-Ac-D-Nal(2)$^1$, D-pF-Phe$^2$, D-Pal(3)$^{3,6}$, Arg$^5$, hArg(CH$_2$)$_3$$^8$, D-Ala$^{10}$] GnRH

[N-Ac-D-Nal(2)$^1$, D-pCl-Phe$^2$, D-Pal(3)$^{3,6}$, Arg$^5$, hArg(CH$_2$CF$_3$)$_2$$^8$, D-Ala$^{10}$] GnRH

[N-Ac-D-Nal(2)$^1$, D-pCl-Phe$^2$, D-Trp$^{3,6}$, Arg$^5$, hArg(CH$_2$)$_3$$^8$, D-Ala$^{10}$] GnRH

[N-Ac-D-Nal(2)$^1$, D-pCl-Phe$^2$, D-Trp$^{3,6}$, Arg$^5$, hArg(CH$_2$CF$_3$)$_2$$^8$, D-Ala$^{10}$] GnRH

[N-Ac-D-Nal(2)$^1$, D-pF-Phe$^2$, D-Pal(3)$^{3,6}$, hArg(Et)$_2$$^{5,8}$, D-Ala$^{10}$] GnRH

[N-Ac-D-Nal(2)$^1$, D-pCl-Phe$^2$, D-Pal(3)$^{3,6}$, hArg(Bu)$^{5,8}$, D-Ala$^{10}$] GnRH

[N-Ac-D-Nal(2)$^1$, D-pCl-Phe$^2$, D-Pal(3)$^3$, D-Tyr$^6$, hArg(CH$_2$CF$_3$)$_2$$^{5,8}$, D-Ala$^{10}$] GnRH

[N-Ac-D-Nal(2)$^1$, D-pCl-Phe$^2$, D-Pal(3)$^{3,6}$, hArg(Et)$_2$$^8$, D-Ala$^{10}$] GnRH

[N-Ac-D-Nal(2)$^1$, D-pCl-Phe$^2$, D-Pal(3)$^{3,6}$, hArg(CH$_2$)$_3$$^8$, D-Ala$^{10}$] GnRH

[N-Ac-D-Nal(2)$^1$, D-pCl-Phe$^2$, D-Pal(3)$^{3,6}$, hArg(Bu)$^8$, D-Ala$^{10}$] GnRH

[N-Ac-D-Nal(2)$^1$, D-pCl-Phe$^2$, D-Pal(3)$^{3,6}$ Pal(3)$^5$, hArg(CH$_2$CF$_3$)$_2$$^8$, D-Ala$^{10}$] GnRH

[N-Ac-D-Nal(2)$^1$, D-pCl-Phe$^2$, D-Trp$^{3,6}$, hArg(Et)$_2$$^8$, D-Ala$^{10}$] GnRH

[N-Ac-D-Nal(2)$^1$, D-pCl-Phe$^2$, D-Trp$^{3,6}$, hArg(CH$_2$)$_3$$^8$, D-Ala$^{10}$] GnRH

[N-Ac-D-Nal(2)$^1$, D-pCl-Phe$^2$, D-Trp$^{3,6}$, hArg(Bu)$^8$, D-Ala$^{10}$] GnRH

[N-Ac-D-Nal(2)$^1$, D-pCl-Phe$^2$, D-Trp$^{3,6}$, hArg(CH$_2$CF$_3$)$_2$$^8$, D-Ala$^{10}$] GnRH

[N-Ac-D-Nal(2)$^1$, D-pCl-Phe$^2$, D-Pal(3)$^3$, D-hArg(Et)$_2$$^6$, hArg(Et$_2$)$^8$, D-Ala$^{10}$] GnRH

[N-Ac-D-Nal(2)$^1$, D-pCl-Phe$^2$, D-Pal(3)$^3$, D-hArg(CH$_2$)$_3$$^6$, hArg(CH$_2$)$_3$$^8$, D-Ala$^{10}$] GnRH

[N-Ac-D-Nal(2)$^1$, D-pCl-Phe$^2$, D-Pal(3)$^3$, D-hArg(Bu)$^6$, hArg(Bu)$_1$$^8$, D-Ala$^{10}$] GnRH

[N-Ac-D-Nal(2)$^1$, D-pF-Phe$^2$, D-Pal(3)$^3$, D-hArg(Et)$_2$$^6$, hArg(Et)$_2$$^8$, D-Ala$^{10}$] GnRH

[N-Ac-D-Nal(2)$^1$, D-pF-Phe$^2$, D-Pal(3)$^3$, D-hArg(Bu)$^6$, hArg(CH$_2$CF$_3$)$_2$$^8$, D-Ala$^{10}$] GnRH

[N-Ac-D-Nal(2)$^1$, D-pF-Phe$^2$, D-Pal(3)$^3$, D-hArg(CH$_2$CF$_3$)$_2$$^6$, hArg(Et)$_2$$^8$, D-Ala$^{10}$] GnRH

[N-Ac-D-Nal(2)$^1$, D-pCl-Phe$^2$, D-Trp$^3$, D-hArg(Et)$_2$$^6$, hArg(Et)$_2$$^8$, D-Ala$^{10}$] GnRH

[N-Ac-D-Nal(2)$^1$, D-pCl-Phe$^2$, D-Trp$^3$, D-hArg(CH$_2$)$_3$$^6$, hArg(CH$_2$)$_3$$^8$, D-Ala$^{10}$] GnRH

Ac-D-Na(2) D-Phe-(4Cl) D-Pal(3) Ser Tyr D-Lys(A$_2$pr(Ac)$_2$) Leu Arg Pro D-Ala-NH$_2$

Ac-D-Na(2) D-Phe-(4Cl) D-Pal(3) Ser Tyr D-Lys(A$_2$pr(For)$_2$) Leu Arg D-Ala-NH

Ac-D-Na(2) D-Phe-(4Cl) D-Pal(3) Ser Tyr D-Lys(A$_2$pr(For)$_2$) Leu Arg Pro D-Ala-NH$_2$

Ac-D-Na(2) D-Phe-(4Cl) D-Pal(3) Ser Tyr D-Lys(A$_2$bu(Prl)$_2$) Leu Arg Pro D-Ala-NH

Ac-D-Na(2) D-Phe-(4Cl) D-Trp Ser Arg D-Lys(A$_2$pr(For)$_2$) Leu Arg Pro D-Ala-NH

Ac-D-Na(2) D-Phe-(4Cl) D-Pal(3) Ser Tyr D-Lys(A$_2$pr(EtCar)$_2$) Leu Arg Pro D-Ala-NH

Ac-D-Na(2) D-Phe-(4Cl) D-Pal(3) Ser Tyr D-Lys(A$_2$pr(CHC)$_2$) Leu Arg Pro D-Ala-NH

Ac-D-Na(2) D-Phe-(4Cl) D-Pal(3) Ser Tyr D-Lys(A$_2$bu(Car)$_2$) Leu Arg Pro D-Ala-NH

Ac-D-Na(2) D-Phe-(4Cl) D-Pal(3) Ser Tyr D-Lys(A$_2$pr(BZ)$_2$) Leu Arg Pro D-Ala-NH

Ac-D-Na(2) D-Phe-(4Cl) D-Pal(3) Ser Tyr D-Lys(A$_2$bu(Ac)$_2$) Leu Arg Pro D-Ala-NH

Ac-D-Na(2) D-Phe-(4Cl) D-Pal(3) Ser Tyr D-Lys(A$_2$bu(CHC)$_2$) Leu Arg Pro D-Ala-NH

Ac-D-Na(2) D-Phe-(4Cl) D-Pal(3) Ser Tyr D-Lys(A$_2$bu(LAU)$_2$) Leu Arg Pro D-Ala-NH

Ac-D-Na(2) D-Phe-(4Cl) D-Pal(3) Ser Tyr D-Lys(A$_2$pr(Car)$_2$) Leu Arg Pro D-Ala-NH

[N-Ac-D-pCl-Phe$^1$, D-pCl-Phe$^2$, D-Trp$^3$, D-Arg$^6$, D-Ala$^{10}$]LHRH

[N-Ac-D-Nal(2)$^1$, D-pF-Phe$^2$, D-Trp$^3$, D-Arg$^6$] LHRH

[N-Ac-D-pCl-Phe$^1$, D-pCl-Phe$^2$, D-Trp$^3$, D-hArg(Me$_2$)$^6$, D-Ala$^{10}$]LHRH

[N-Ac-D-Nal(2)$^1$, D-pF-Phe$^2$, D-Trp$^3$, D-hArg(Me$_2$)$^6$] LHRH

[N-Ac-D-pCl-Phe$^1$, D-pCl-Phe$^2$, D-Trp$^3$, D-hArg(Et$_2$)$^6$, D-Ala$^{10}$]LHRH

[N-Ac-D-pCl-Phe$^2$, D-pCl -Phe$^2$, D-Trp$^3$, D-hArg(Et$_2$)$^6$] LHRH

[N-Ac-D-Nal(2)$^1$, D-pF-Phe$^2$, D-Trp$^3$, D-hArg(Et$_2$)$^6$] LHRH

[N-Ac-D-Nal(2)$^1$, D-pCl-Phe$^2$, D-Trp$^3$, D-hArg(Et$_2$)$^6$] LHRH

[N-Ac-D-Nal(2)$^1$, D-pCl-Phe$^2$, D-Trp$^3$, D-hArg(Et$_2$)$^6$, D-Ala$^{10}$]LHRH

[N-Ac-D-pCl-Phe$^1$, D-pCl-Phe$^2$, D-Trp$^3$, D-hArg(Pr$_2$)$^6$, D-Ala$^{10}$]LHRH

[N-Ac-D-pCl-Phe$^1$, D-pCl-Phe$^2$, D-Trp$^3$, D-hArg(Pr$_2$)$^6$] LHRH

[N-Ac-D-Nal(2)$^1$, D-pF-Phe$^2$, D-Trp$^3$, D-hArg(Pr$_2$)$^6$LHRH

[D-Phe$^2$] LHRH

[D-Phe$^{2,6}$] LHRH

[Ac-Pro$^1$, D-Phe$^2$, D-Trp$^6$] LHRH

[Ac-D-Phe$^1$, D-(pCl)Phe$^2$, D-Trp$^{3,6}$] LHRH

[Ac-$\Delta^3$Pro$^1$, D-(pF)Phe$^2$, D-Trp$^{3,6}$] LHRH

[Ac-D-(pCl)Phe$^1$, D-(pCl)Phe$^2$, D-Trp$^3$, D-Arg$^6$, D-Arg$^{10}$] LHRH and

[Ac-D-Nal(2)$^1$, D-(pCl)Phe$^2$, D-Trp$^3$, D-hArg(Et$_2$)$^6$, D-Arg$^{10}$] LHRH.

20. The method according to claim 15 wherein the therapeutic effective amount of the LHRH analog is sufficient to maintain blood serum concentrations of testosterone at about 2 to 10 nmol/l, FSH at about 2 to 10 IU/l and LH at about 2 to 10 IU/l.

21. The method according to claim 20 wherein the LHRH analog is administered by topical administration.

22. The method according to claim 21 wherein the LHRH analog is applied to the skin of the armpit region.

23. The method according to claim 20 wherein the LHRH analog is administered transdermally.

24. The method according to claim 20 wherein the LHRH analog is administered transmucosally.

25. The method according to claim 20 wherein the LHRH analog is administered by subcutaneous or intramuscular injection.

26. The method according to claim 20 wherein the LHRH analog is administered by subdermal implant.

27. The method according to claim 20 wherein the LHRH analog is administered orally.

28. A method of treatment of male-pattern baldness which comprises the administration of a therapeutically effective amount of a first non-steroidal, polypeptide analog of LHRH capable of suppressing testosterone formation in patients in the active phases of male pattern baldness and a therapeutically effective amount of a second non-steroidal, polypeptide analog of LHRH capable of suppressing testosterone formation in patients in the active phases of male pattern baldness.

29. The method according to claim 28 wherein the first LHRH analog is an LHRH agonist and the second LHRH analog is an LHRH agonist.

30. The method according to claim 28 wherein the first LHRH analog is an LHRH antagonist and the second LHRH analog is an LHRH antagonist.

31. The method according to claim 28 wherein the first LHRH is an LHRH agonist and the second LHRH analog is an LHRH antagonist.

32. The method according to claim 29 wherein the first and second LHRH agonist are selected from the group consisting of

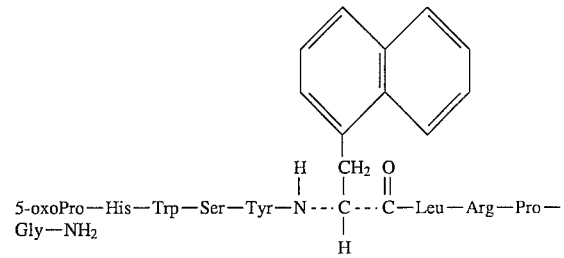

5-oxoPro—His—Trp—Ser—Tyr—N---C---C—Leu—Arg—Pro—Gly—NH$_2$ 5-oxoPro-His-Trp-Ser-Tyr-D-Leu-Leu-Arg-Pro-NHC$_2$H$_5$ 5-oxoPro-His-Trp-Ser-Tyr-D-Ser(t-Bu)-Leu-Arg-Pro-NHNHCONH$_2$ 5-oxoPro-His-Trp-Ser-Tyr-D-Ser(t-Bu)-Leu-Arg-Pro-NHC$_2$H$_5$ 5-oxoPro-His-Trp-Ser-Tyr-N$^t$-benzyl-His-Leu-Arg-Pro-NHC$_2$H$_5$ 5-oxoPro-His-Trp-Ser-Tyr-Gly-Leu-Arg-Pro-Gly-NH$_2$

[D-Gly(—CH$_2$—S—Bu$^t$)$^6$, Pro$^9$-NHEt] LHRH

[D-Ser(Bu$^t$)$^6$, Pro$^9$-NHEt] LHRH

[D-Gly(—CH$_2$—O—Bu$_t$)$^6$, Pro$^9$-NHEt] LHRH

[D-Gly(—H)$^6$, Cys(Bu$^t$)$^7$, Pro$^9$-NHEt ] LHRH

[D-Gly-(—CH$_2$—O—Bu$^t$)$^6$, Cys(Bu$^t$)$^7$, Pro$^9$-NHEt] LHRH

[D-Tmo$^6$] LHRH

[D-Trp$^6$, Pro$^9$-NHEt] LHRH

[D-Cha$^6$] LHRH

[D-Pfp$^6$] LHRH

[D-Nal(1)$^6$] LHRH

[D-Nal(2)$^6$] LHRH

[D-Mtf$^6$] LHRH

[D-Ptf$^6$] LHRH

[D-Tmp$^6$] LHRH

[D-Arg$^6$] LHRH

[D-Arg$^6$, Pro$^9$-NHEt] LHRH

[D-hArg$^6$ (Et$_2$)$^6$, Pro$^9$-NHEt] LHRH

[D-Dca$^6$] LHRH

[D-Phe$^6$] LHRH

[D-Ser(Bu$^t$)$^6$, Azgly$^{10}$] LHRH

[D-Nal(2)$^6$, aza-Gly$^{10}$] LHRH

[D-Nal(2)$^6$] LHRH

[D-Nal(2)$^6$, Pro$^9$-NHEt] LHRH

[D-Ser(Bu$^t$)$^6$, aza-Gly$^{10}$] LHRH

[D-Trp$^6$] LHRH

[D-Trp$^6$, Pro$^9$-NHEt] LHRH

[D-His(Bzl)$^6$, Pro$^9$-NHEt] LHRH and

[D-Nal(2)$^6$, aza-Gly$^{10}$] LHRH.

33. The method according to claim 30 wherein the first and second LHRH antagonist are selected from the group consisting of N$^G$, N$^{G'}$-dialkyl-D-homoarginines

[N-Ac-D-Nal(2)$^1$, D-pCl-Phe$^2$, D-TrP$^3$, D-hArg(Et$_2$)$^6$, D-Ala$^{10}$] LHRH

[N-Ac-D-Nal(2)$^1$, D-pClPhe$^2$, D-Pal(3)$^3$, D-hArg(Et$_2$)$^6$, L-hArg(Et$_2$)$^8$, D-Ala$^{10}$] LHRH,

[Ac-D-Nal(2)-D-pCl-Phe-D-Trp-Ser-Tyr-D-Ser (Rha)Leu-Arg-Pro-AzGly-NH$_2$] LHRH, (Ac-D-Nal(2)$^1$, D-Phe(4Cl)$^2$, D-Pal(3)$^3$, D-Cit$^6$, D-Ala$^{10}$) LHRH,

Nal-Glu (Ac-D-Nal(2)1, D-Phe(4Cl)2, D-Pal 3, Arg5, D-Glu$^6$ (AA), D-Ala$^{10}$)

(Ac-D-Nal(2)$^1$, D-pCl-Phe$^2$, D-Trp$^3$, D-hArg(Et$_2$)$^6$, D-Ala$^{10}$), (Ac-Δ3Prol, 4F-D-Phe2, D-Trp3, 6)

(Ac-DNal-DCpa-DPal-Ser-Arg-D-2-amino-5-oxo-5-(4-methoxyphenol) pentanoic acid-Leu-Arg-Pro-DAla-NH$_2$),

[Ac-DNal$^1$, DCpa$^2$, Dpal$^3$, Lys$^5$(Atz), DLys$^6$ (Atz), ILys$^8$, DAla$^{10}$] LHRH,

[Ac-DNal$^1$, DCpa$^2$, DPal$^3$, Aph$^5$(Atz) , DAph$^6$(Atz), ELys$^8$, DAla$^{10}$]-LHRH,

[N-Ac-D-2-Nal$^1$, DpClPhe$^2$, D-3-Pal$^3$, NicLys$^5$, D-NicLys$^6$, ILys$^8$, D-Ala$^{10}$] LHRH,

[N-Ac-D-2-Nal$^1$, D-Phe$^2$, D-3-Pal$^3$, NicLys$^5$, D-NicLys$^6$, ILys$^8$, D-Ala$^{10}$] LHRH

[N-Ac-D-Nal(2)$^1$, D-pF-Phe$^2$, D-Trp$^3$, D-Arg$^6$] GnRH

[N-Ac-D-Nal(2)$^1$, D-pCl-Phe$^2$, D-Pal(3)$^3$, Arg$^5$, D-Glu (AA)$^6$, D-Ala$^{10}$] GnRH

[N-Ac-D-Nal(2)$^1$, D-pCl-Phe$^2$, D-Trp$^3$, D-hArg(Et)$_2$$^6$, D-Ala$^{10}$] GnRH

[N-Ac-D-Nal(2)$^1$, D-pCl-Phe$^2$, D-Pal(3)$^3$, D-hArg(Et)$_2$$^6$, Phe$^7$, D-Ala$^{10}$] GnRH

[N-Ac-D-Nal(2)$^1$, D-pCl-Phe$^2$, D-Trp$^3$, D-hArg(CH$_2$)$_3$$^6$, D-Ala$^{10}$] GnRH

[N-Ac-D-Nal(2)$^1$, D-pCl-Phe$^2$, D-Pal(3)$^{3,6}$, Arg$^5$, hArg(Et$_2$)$^8$, D-Ala$^{10}$] GnRH

[N-Ac-D-Nal(2)$^1$, D-pCl-Phe$^2$, D-Pal(3)$^{3,6}$, Arg$^5$, hArg(CH$_2$)$_3$$^8$, D-Ala$^{10}$] GnRH

[N-Ac-D-Nal(2)$^1$, D-pF-Phe$^2$, D-Pal(3)$^{3,6}$, Arg$^5$, hArg(CH$_2$)$_3$$^8$, D-Ala$^{10}$] GnRH

[N-Ac-D-Nal(2)$^1$, D-pCl-Phe$^2$, D-Pal(3)$^{3,6}$, Arg$^5$, hArg(CH$_2$CF$_3$)$_2$$^8$, D-Ala$^{10}$] GnRH

[N-Ac-D-Nal(2)$^1$, D-pCl-Phe$^2$, D-Trp$^{3,6}$, Arg$^5$, hArg(CH$_2$)$_3$$^8$, D-Ala$^{10}$] GnRH

[N-Ac-D-Nal(2)$^1$, D-pCl-Phe$^2$, D-Trp$^{3,6}$, Arg$^5$, hArg(CH$_2$CF$_3$)$_2$$^8$, D-Ala$^{10}$] GnRH

[N-Ac-D-Nal(2)$^1$, D-pF-Phe$^2$, D-Pal(3)$^{3,6}$, hArg(Et)$_2$$^{5,8}$, D-Ala$^{10}$] GnRH

[N-Ac-D-Nal(2)$^1$, D-pCl-Phe$^2$, D-Pal(3)$^{3,6}$, hArg(Bu)$^{5,8}$, D-Ala$^{10}$] GnRH

[N-Ac-D-Nal(2)$^1$, D-pCl-Phe$^2$, D-Pal(3)$^3$, D-Tyr$^6$, hArg(CH$_2$CF$_3$)$_2$$^{5,8}$, D-Ala$^{10}$] GnRH

[N-Ac-D-Nal(2)$^1$, D-pCl-Phe$^2$, D-Pal(3)$^{3,6}$, hArg(Et)$_2$$^8$, D-Ala$^{10}$] GnRH

[N-Ac-D-Nal(2)$^1$, D-pCl-Phe$^2$, D-Pal(3)$^{3,6}$, hArg(CH$_2$)$_3$$^8$, D-Ala$^{10}$] GnRH

[N-Ac-D-Nal(2)$^1$, D-pCl-Phe$^2$, D-Pal(3)$^{3,6}$, hArg(Bu)$^8$, D-Ala$^{10}$] GnRH

[N-Ac-D-Nal(2)$^1$, D-pCl-Phe$^2$, D-Pal(3)$^{3,6}$ Pal(3)$^5$, hArg(CH$_2$CF$_3$)$_2$$^8$, D-Ala$^{10}$] GnRH

[N-Ac-D-Nal(2)$^1$, D-pCl-Phe$^2$, D-Trp$^{3,6}$, hArg(Et)$_2$$^8$, D-Ala$^{10}$] GnRH

[N-Ac-D-Nal(2)$^1$, D-pCl-Phe$^2$, D-Trp$^{3,6}$, hArg(CH$_2$)$_3$$^8$, D-Ala$^{10}$] GnRH

[N-Ac-D-Nal(2)$^1$, D-pCl-Phe$^2$, D-Trp$^{3,6}$, hArg(Bu)$^8$, D-Ala$^{10}$] GnRH

[N-Ac-D-Nal(2)$^1$, D-pCl-Phe$^2$, D-Trp$^{3,6}$, hArg(CH$_2$CF$_3$)$_2$$^8$, D-Ala$^{10}$] GnRH

[N-Ac-D-Nal(2)$^1$, D-pCl-Phe$^2$, D-Pal(3)$^3$, D-hArg(Et)$_2$$^6$, hArg(Et)$_2$$^8$, D-Ala$^{10}$] GnRH

[N-Ac-D-Nal(2)$^1$, D-pCl-Phe$^2$, D-Pal(3)$^3$, D-hArg(CH$_2$)$_3$$^6$, hArg(CH$_2$)$_3$$^8$, D-Ala$^{10}$] GnRH

[N-Ac-D-Nal(2)$^1$, D-pCl-Phe$^2$, D-Pal(3)$^3$, D-hArg(Bu)$^6$, hArg(Bu)$_1$$^8$, D-Ala$^{10}$] GnRH

[N-Ac-D-Nal(2)$^1$, D-pF-Phe$^2$, D-Pal(3)$^3$, D-hArg(Et)$_2$$^6$, hArg(Et)$_2$$^8$, D-Ala$^{10}$] GnRH

[N-Ac-D-Nal(2)$^1$, D-pF-Phe$^2$, D-Pal(3)$^3$, D-hArg(Bu)$^6$, hArg(CH$_2$CF$_3$)$_2$$^8$, D-Ala$^{10}$] GnRH

[N-Ac-D-Nal(2)$^1$, D-pF-Phe$^2$, D-Pal(3)$^3$, D-hArg(CH$_2$CF$_3$)$_2$$^6$, hArg(Et)$_2$$^8$, D-Ala$^{10}$] GnRH

[N-Ac-D-Nal(2)$^1$, D-pCl-Phe$^2$, D-Trp$^3$, D-hArg(Et)$_2$$^6$, hArg(Et)$_2$$^8$, D-Ala$^{10}$] GnRH

[N-Ac-D-Nal(2)$^1$, D-pCl-Phe$^2$, D-Trp$^3$, D-hArg(CH$_2$)$_3$$^6$, hArg(CH$_2$)$_3$$^8$, D-Ala$^{10}$] GnRH

Ac-D-Na(2) D-Phe-(4Cl) D-Pal(3) Ser Tyr D-Lys(A$_2$pr(Ac)$_2$) Leu Arg Pro D-Ala-NH$_2$

Ac-D-Na(2) D-Phe-(4Cl) D-Pal(3) Ser Tyr D-Lys(A$_2$pr(For)$_2$) Leu Arg Pro D-Ala-NH

Ac-D-Na(2) D-Phe-(4Cl) D-Pal(3) Ser Tyr D-Lys(A$_2$bu(For)$_2$) Leu Arg Pro D-Ala-NH$_2$

Ac-D-Na(2) D-Phe-(4Cl) D-Pal(3) Ser Tyr D-Lys(A$_2$bu(Prl)$_2$) Leu Arg Pro D-Ala-NH

Ac-D-Na(2) D-Phe-(4Cl) D-Trp Ser Arg D-Lys(A$_2$pr(For)$_2$) Leu Arg Pro D-Ala-NH

Ac-D-Na(2) D-Phe-(4Cl) D-Pal(3) Ser Tyr D-Lys(A$_2$pr(EtCar)$_2$) Leu Arg Pro D-Ala-NH

Ac-D-Na(2) D-Phe-(4Cl) D-Pal(3) Ser Tyr D-Lys(A$_2$pr(CHC)$_2$) Leu Arg Pro D-Ala-NH

Ac-D-Na(2) D-Phe-(4Cl) D-Pal(3) Ser Tyr D-Lys(A$_2$pr(Car)$_2$) Leu Arg Pro D-Ala-NH

Ac-D-Na(2) D-Phe-(4Cl) D-Pal(3) Ser Tyr D-Lys (A$_2$pr(BZ)$_2$) Leu Arg Pro D-Ala-NH

Ac-D-Na(2) D-Phe-(4Cl) D-Pal(3) Ser Tyr D-Lys(A$_2$bu(Ac)$_2$) Leu Arg Pro D-Ala-NH

Ac-D-Na(2) D-Phe-(4Cl) D-Pal(3) Ser Tyr D-Lys(A$_2$bu(CHC)$_2$) Leu Arg Pro D-Ala-NH

Ac-D-Na(2) D-Phe-(4Cl) D-Pal(3) Ser Tyr D-Lys(A$_2$bu(LAU)$_2$) Leu Arg Pro D-Ala-NH

Ac-D-Na(2) D-Phe-(4Cl) D-Pal(3) Ser Tyr D-Lys(A$_2$pr(Car)$_2$) Leu Arg Pro D-Ala-NH

[N-Ac-D-pCl-Phe $^1$, D-pCl-Phe$^2$, D-Trp$^3$, D-Arg$^6$, D-Ala$^{10}$]LHRH

[N-Ac-D-Nal(2)$^1$, D-pF-Phe$^2$, D-Trp$^3$, D-Arg$^6$]LHRH

[N-Ac-D-pCl-Phe$^1$, D-pCl-Phe$^2$, D-Trp$^3$, D-hArg(Me$_2$)$^6$, D-Ala$^{10}$]LHRH

[N-Ac-D-Nal(2)$^1$, D-pF-Phe$^2$, D-Trp$^3$, D-hArg(Me$_2$)$^6$] LHRH

[N-Ac-D-pCl-Phe$^1$, D-pCl-Phe$^2$, D-Trp$^3$, D-hArg(Et$_2$)$^6$, D-Ala$^{10}$]LHRH

[N-Ac-D-pCl-Phe$^1$, D-pCl-Phe$^2$, D-Trp$^3$, D-hArg(Et$_2$)$_6$] LHRH

[N-Ac-D-Nal(2)$^1$, D-pF-Phe$^2$, D-Trp$^3$, D-hArg(Et$_2$)$^6$] LHRH

[N-Ac-D-Nal(2)$^1$, D-pCl-Phe$^2$, D-Trp$^3$, D-hArg(Et$_2$)$^6$] LHRH

[N-Ac-D-Nal(2)$^1$, D-pCl-Phe$^2$, D-Trp$^3$, D-hArg(Et$_2$)$^6$, D-Ala$^{10}$]LHRH

[N-Ac-D-pCl-Phe$^1$, D-pCl-Phe$^2$, D-Trp$^3$, D-hArg(Pr$_2$)$^6$, D-Ala$^{10}$]LHRH

[N-Ac-D-pCl-Phe$^1$, D-pCl-Phe$^2$, D-Trp$^3$, D-hArg(Pr$_2$)$^6$] LHRH

[N-Ac-D-Nal(2)$^1$, D-pF-Phe$^2$, D-Trp$^3$, D-hArg(Pr$_2$)$^6$]LHRH

[D-Phe$^2$] LHRH

[D-Phe$^{2,6}$] LHRH

[Ac-Pro$^1$, D-Phe$^2$, D-Trp$^6$] LHRH

[Ac-D-Phe$^1$, D-(pCl)Phe$^2$, D-Trp$^{3,6}$] LHRH

[Ac-Δ$^3$Pro$^1$, D-(pF)Phe$^2$, D-Trp$^{3,6}$] LHRH

[Ac-D-(pCl)Phe$^1$, D-(pCl)Phe$^2$, D-Trp$^3$, D-Arg$^6$, D-Arg$^{10}$] LHRH and

[Ac-D-Nal(2)$^1$, D-(pCl)Phe$^2$, D-Trp$^3$, D-hArg(Et$_2$)$^6$, D-Arg$^{10}$] LHRH.

34. The method according to claim 31 wherein the LHRH agonist is selected from the group consisting of

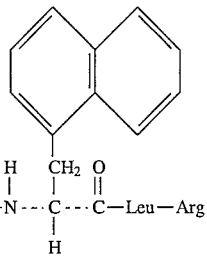

5-oxoPro—His—Trp—Ser—Tyr—N---C---C—Leu—Arg—Pro—Gly—NH$_2$ 5-oxoPro-His-Trp-Ser-Tyr-D-Leu-Leu-Arg-Pro-NHC$_2$H$_5$ 5-oxoPro-His-Trp-Ser-Tyr-D-Ser(t-Bu)-Leu-Arg-Pro-NHNHCONH$_2$ 5-oxoPro-His-Trp-Ser-Tyr-D-Ser(t-Bu)-Leu-Arg-Pro-NHC$_2$H$_5$ 5-oxoPro-His-Trp-Ser-Tyr-N$^t$-benzyl-His-Leu-Arg-Pro-NHC$_2$H$_5$ 5-oxoPro-His-Trp-Ser-Tyr-Gly-Leu-Arg-Pro-Gly-Gly-NH$_2$

[D-Gly(—CH$_2$—S—Bu$^t$)$^6$, Pro$^9$-NHEt] LHRH

[D-Ser(Bu$^t$)$^6$, Pro$^9$-NHEt] LHRH

[D-Gly(—CH$_2$—O—Bu$^t$)$^6$, Pro$^9$-NHEt] LHRH

[D-Gly(—H)$^6$, Cys(Bu$^t$)$^7$, Pro$^9$-NHEt] LHRH

[D-Gly-(—CH$_2$—O—Bu$^t$)$^6$, Cys(Bu$^t$)$^7$, Pro$^9$-NHEt] LHRH

[D-Tmo$^6$] LHRH

[D-Trp$^6$, Pro$^9$-NHEt] LHRH

[D-Cha$^6$] LHRH

[D-Pfp$^6$] LHRH

[D-Nal(1)$^6$] LHRH

[D-Nal(2)$^6$] LHRH

[D-Mtf$^6$] LHRH

[D-Ptf$^6$] LHRH

[D-Tmp$^6$] LHRH

[D-Arg$^6$] LHRH

[D-Arg$^6$, Pro$^9$-NHEt] LHRH

[D-hArg$^6$ (Et$_2$)$^6$, Pro$^9$-NHEt] LHRH

[D-Dca$^6$] LHRH

[D-Phe$^6$] LHRH

[D-Ser(Bu$^t$)$^6$, Azgly$^{10}$] LHRH

[D-Nal(2)$^6$, aza-Gly$^{10}$] LHRH

[D-Nal(2)$^6$] LHRH

[D-Nal(2)$^6$, Pro$^9$-NHEt] LHRH

[D-Ser(Bu$^t$)$^6$, aza-Gly$^{10}$] LHRH

[D-Trp$^6$] LHRH

[D-Trp$^6$, Pro$^9$-NHEt] LHRH

[D-His(Bzl)$^6$, Pro$^9$-NHEt] LHRH and

[D-Nal(2)$^6$, aza-Gly$^{10}$] LHRH and the LHRH antagonist is selected from the group consisting of N$^G$, N$^G$dialkyl-D-homoarginines

[N-Ac-D-Nal(2)$^1$, D-pCl-Phe$^2$, D-Trp$^3$, D-hArg(Et$_2$)$^6$, D-Ala$^{10}$] LHRH

[N-Ac-D-Nal(2)$^1$, D-pClPhe$^2$, D-Pal(3)$^3$, D-hArg(Et$_2$)$^6$, L-hArg(Et$_2$)$^8$, D-Ala$^{10}$] LHRH,

[Ac-D-Nal(2)-D-pCl-Phe-D-Trp-Ser-Tyr-D-Ser(Rha)Leu-Arg-Pro-AzGly-NH$_2$] LHRH, (Ac-D-Nal (2)$^1$, D-Phe(4Cl)$^2$, D-Pal(3)$^3$, D-Cit$^6$, D-Ala$^{10}$) LHRH,

Nal-Glu (Ac-D-Nal(2)1, D-Phe(4Cl)2, D-Pal 3, Arg5, D-Glu$^6$ (AA), D-Ala$^{10}$)

(Ac-D-Nal(2)$^1$, D-pCl-Phe$^2$, D-Trp$^3$, D-hArg(Et2)$^6$, D-Ala$^{10}$), (Ac-Δ3Pro1, 4F-D-Phe2, D-Trp3, 6)

(Ac-DNal-DCpa-DPal-Ser-Arg-D-2-amino-5-oxo-5-(4-methoxyphenol) pentanoic acid-Leu-Arg-Pro-DAla-NH$_2$),

[Ac-DNal$^1$, DCpa$^2$, Dpal$^3$, Lys$^5$(Atz), DLys$^6$ (Atz), ILys$^8$, DAla$^{10}$] LHRH,

[Ac-DNal$^1$, DCpa$^2$, DPal$^3$, Aph$^5$(Atz), DAph$^6$(Atz), ELys$^8$, DAla$^{10}$]-LHRH,

[N-Ac-D-2-Nal$^1$, DpClPhe$^2$, D-3-Pal$^3$, NicLys$^5$, D-NicLys$^6$, ILys$^8$, D-Ala$^{10}$] LHRH,

[N-Ac-D-2-Nal$^1$, D-Phe$^2$, D-3-Pal$^3$, NicLys$^5$, D-NicLys$^5$, D-NicLys$^6$, ILys$^8$, D-Ala$^{10}$] LHRH

[N-Ac-D-Nal(2)$^1$, D-pF-Phe$^2$, D-Trp$^3$, D-Arg$^6$] GnRH

[N-Ac-D-Nal(2)$^1$, D-pCl-Phe$^2$, D-Pal(3)$^3$, Arg$^5$, D-Glu(AA)$^6$, D-Ala$^{10}$] GnRH

[N-Ac-D-Nal(2)$^1$, D-pCl-Phe$^2$, D-Trp$^3$, D-hArg(Et)$_2$$^6$, D-Ala$^{10}$] GnRH

[N-Ac-D-Nal(2)$^1$, D-pCl-Phe$^2$, D-Pal(3)$^3$, D-hArg(Et)$_2$$^6$, Phe$^7$, D-Ala$^{10}$] GnRH

[N-Ac-D-Nal(2)$^1$, D-pCl-Phe$^2$, D-Trp$^3$, D-hArg(CH$_2$)$_3$$^6$, D-Ala$^{10}$] GnRH

[N-Ac-D-Nal(2)$^1$, D-pCl-Phe$^2$, D-Pal(3)$^{3,6}$, Arg$^5$, hArg(Et$_2$)$^8$, D-Ala$^{10}$] GnRH

[N-Ac-D-Nal(2)$^1$, D-pCl-Phe$^2$, D-Pal(3)$^{3,6}$, Arg$^5$, hArg(CH$_2$)$_3$$^8$, D-Ala$^{10}$] GnRH

[N-Ac-D-Nal(2)$^1$, D-pF-Phe$^2$, D-Pal(3)$^{3,6}$, Arg$^5$, hArg(CH$_2$)$_3$$^8$, D-Ala$^{10}$] GnRH

[N-Ac-D-Nal(2)$^1$, D-pCl-Phe$^2$, D-Pal(3)$^{3,6}$, Arg$^5$, hArg(CH$_2$CF$_3$)$_2$$^8$, D-Ala$^{10}$] GnRH

[N-Ac-D-Nal(2)$^1$, D-pCl-Phe$^2$, D-Trp$^{3,6}$, Arg$^5$, hArg(CH$_2$)$_3$$^8$, D-Ala$^{10}$] GnRH

[N-Ac-D-Nal(2)$^1$, D-pCl-Phe$^2$, D-Trp$^{3,6}$, Arg$^5$, hArg(CH$_2$CF$_3$)$_2$$^8$, D-Ala$^{10}$] GnRH

[N-Ac-D-Nal(2)$^1$, D-pF-Phe$^2$, D-Pal(3)$^{3,6}$, hArg(Et)$_2$$^{5,8}$, D-Ala$^{10}$] GnRH

[N-Ac-D-Nal(2)$^1$, D-pCl-Phe$^2$, D-Pal(3)$^{3,6}$, hArg(Bu)$^{5,8}$, D-Ala$^{10}$] GnRH

[N-Ac-D-Nal(2)$^1$, D-pCl-Phe$^2$, D-Pal(3)$^3$, D-Tyr$^6$, hArg(CH$_2$CF$_3$)$_2$$^{5,8}$, D-Ala$^{10}$] GnRH

[N-Ac -D-Nal(2)$^1$, D-pCl-Phe$^2$, D-Pal(3)$^{3,6}$, hArg(Et)$_2$$^8$, D-Ala$^{10}$] GnRH

[N-Ac-D-Nal(2)$^1$, D-pCl-Phe$^2$, D-Pal(3)$^{3,6}$, hArg(CH$_2$)$_3$$^8$, D-Ala$^{10}$] GnRH

[N-Ac-D-Nal(2)$^1$, D-pCl-Phe$^2$, D-Pal(3)$^{3,6}$, hArg(Bu)$^8$, D-Ala$^{10}$] GnRH

[N-Ac-D-Nal(2)$^1$, D-pCl-Phe$_2$, D-Pal(3)$^{3,6}$ Pal (3)$^5$, hArg(CH$_2$CF$_3$)$_2$$^8$, D-Ala$^{10}$] GnRH

[N-Ac-D-Nal(2)$^1$, D-pCl-Phe$^2$, D-Trp$^{3,6}$, hArg(Et)$_2$$^8$, D-Ala$^{10}$] GnRH

[N-Ac-D-Nal(2)$^1$, D-pCl-Phe$^2$, D-Trp$^{3,6}$, hArg(CH$_2$)$_3$$^8$, D-Ala$^{10}$] GnRH

[N-Ac-D-Nal(2)$^1$, D-pCl-Phe$^2$, D-Trp$^{3,6}$, hArg(Bu)$^8$, D-Ala$^{10}$] GnRH

[N-Ac-D-Nal(2)$^1$, D-pCl-Phe$^2$, D-Trp$^{3,6}$, hArg(CH$_2$CF$_3$)$_2$$^8$, D-Ala$^{10}$] GnRH

[N-Ac-D-Nal(2)$^1$, D-pCl-Phe$^2$, D-Pal(3)$^3$, D-hArg(Et)$_2$$^6$, hArg(Et)$_2$$_8$, D-Ala$^{10}$] GnRH

[N-Ac-D-Nal(2)$^1$, D-pCl-Phe$^2$, D-Pal(3)$^3$, D-hArg(CH$_2$)$_3$$^6$, hArg(CH$_2$)$_3$$^8$, D-Ala$^{10}$ ] GnRH

[N-Ac-D-Nal(2)$^1$, D-pCl-Phe$^2$, D-Pal(3)$^3$, D-hArg(Bu)$^6$, hArg(Bu)$_1$$^8$, D-Ala$^{10}$] GnRH

[N-Ac-D-Nal(2)$^1$, D-pF-Phe$^2$, D-Pal(3)$^3$, D-hArg(Et)$_2$$^6$, hArg(Et)$_2$$^8$, D-Ala$^{10}$] GnRH

[N-Ac-D-Nal(2)$^1$, D-pF-Phe$^2$, D-Pal(3)$^3$, D-hArg(Bu)$_6$, hArg(CH$_2$CF$_3$)$_2$$^8$, D-Ala$^{10}$] GnRH

[N-Ac-D-Nal(2)$^1$, D-pF-Phe$^2$, D-Pal(3)$^3$, D-hArg(CH$_2$CF$_3$)$_2$$^6$, hArg(Et)$_2$$^8$, D-Ala$^{10}$] GnRH

[N-Ac-D-Nal(2)$^1$, D-pCl-Phe$^2$, D-Trp$^3$, D-hArg(Et)$_2$$^6$, hArg(Et)$_2$$^8$, D-Ala$^{10}$] GnRH

[N-Ac-D-Nal(2)$^1$, D-pCl-Phe$^2$, D-Trp$^3$, D-hArg(CH$_2$)$_3$$^6$, hArg(CH$_2$)$_3$$^8$, D-Ala$^{10}$] GnRH

Ac-D-Na(2)  D-Phe-(4Cl)  D-Pal(3)  Ser  Tyr D-Lys(A$_2$pr(Ac)$_2$) Leu Arg Pro D-Ala-NH$_2$

Ac-D-Na(2)  D-Phe-(4Cl)  D-Pal(3)  Ser  Tyr D-Lys(A$_2$pr(For)$_2$) Leu Arg Pro D-Ala-NH

Ac-D-Na(2)  D-Phe-(4Cl)  D-Pal(3)  Ser  Tyr D-Lys(A$_2$bu(For)$_2$) Leu Arg Pro D-Ala-NH$_2$

Ac-D-Na(2)  D-Phe-(4Cl)  D-Pal(3)  Ser  Tyr D-Lys(A$_2$bu(Prl)$_2$) Leu Arg Pro D-Ala-NH

Ac-D-Na(2)  D-Phe-(4Cl)  D-Trp  Ser  Arg D-Lys(A$_2$pr(For)$_2$) Leu Arg Pro D-Ala-NH

Ac-D-Na(2)  D-Phe-(4Cl)  D-Pal(3)  Ser  Tyr D-Lys(A$_2$pr(EtCar)$_2$) Leu Arg Pro D-Ala-NH

Ac-D-Na(2)  D-Phe-(4Cl)  D-Pal(3)  Ser  Tyr D-Lys(A$_2$pr(CHC)$_2$) Leu Arg Pro D-Ala-NH

Ac-D-Na(2)  D-Phe-(4Cl)  D-Pal(3)  Ser  Tyr D-Lys(A$_2$bu(Car)$_2$) Leu Arg Pro D-Ala-NH

Ac-D-Na(2)  D-Phe-(4Cl)  D-Pal(3)  Ser  Tyr D-Lys(A$_2$pr(BZ)$_2$) Leu Arg Pro D-Ala-NH

Ac-D-Na(2)  D-Phe-(4Cl)  D-Pal(3)  Ser  Tyr D-Lys(A$_2$bu(Ac)$_2$) Leu Arg Pro D-Ala-NH

Ac-D-Na(2)  D-Phe-(4Cl)  D-Pal(3)  Ser  Tyr D-Lys(A$_2$bu(CHC)$_2$) Leu Arg Pro D-Ala-NH

Ac-D-Na(2)  D-Phe-(4Cl)  D-Pal(3)  Ser  Tyr D-Lys(A$_2$bu(LAU)$_2$) Leu Arg Pro D-Ala-NH

Ac-D-Na(2)  D-Phe-(4Cl)  D-Pal(3)  Ser  Tyr D-Lys(A$_2$pr(Car)$_2$) Leu Arg Pro D-Ala-NH

[N-Ac-D-pCl-Phe$^1$, D-pCl -Phe$^2$, D-Trp$^3$, D-Arg$^6$, D-Ala$^{10}$] LHRH

[N-Ac-D-Nal(2)$^1$, D-pF-Phe$^2$, D-Trp$^3$, D-Arg$^6$]LHRH

[N-Ac-D-pCl-Phe$^1$, D-pCl-Phe$^2$, D-Trp$^3$, D-hArg(Me$_2$)$^6$, D-Ala$^{10}$] LHRH

[N-Ac-D-Nal(2)$^1$, D-pF-Phe$^2$, D-Trp$^3$, D-hArg(Me$_2$)$^6$] LHRH

[N-Ac-D-pCl-Phe$^1$, D-pCl-Phe$^2$, D-Trp$^3$, D-hArg(Et$_2$)$^6$, D-Ala$^{10}$] LHRH

[N-Ac-D-pCl-Phe$^1$, D-pCl-Phe$^2$, D-Trp$^3$, D-hArg(Et$_2$)$^6$] LHRH

[N-Ac-D-Nal(2)$^1$, D-pF-Phe$^2$, D-TrP$^3$, D-hArg(Et$_2$)$^6$] LHRH

[N-Ac-D-Nal(2)$^1$, D-pCl-Phe$^2$, D-TrP$^3$, D-hArg(Et$_2$)$^6$] LHRH

[N-Ac-D-Nal(2)$^1$, D-pCl-Phe$^2$, D-Trp$^3$, D-hArg(Et$_2$)$^6$, D-Ala$^{10}$]LHRH

[N-Ac-D-pCl-Phe$^1$, D-pCl-Phe$^2$, D-Trp$^3$, D-hArg(Pr$_2$)$^6$, D-Ala$^{10}$]LHRH

[N-Ac-D-pCl-Phe$^1$, D-pCl-Phe$^2$, D-Trp$^3$, D-hArg(Pr$_2$)$^6$] LHRH

[N-Ac-D--Nal(2)$^1$, D-pF-Phe$^2$, D-Trp$^3$, D-hArg(Pr$_2$)$^6$LHRH

[D-Phe$^2$] LHRH

[D-Phe$^{2,6}$] LHRH

[Ac-Pro$^1$, D-Phe$^2$, D-Trp$^6$] LHRH

[Ac-D-Phe$^1$, D-(pCl)Phe$^2$, D-Trp$^{3,6}$] LHRH

[Ac-Δ$^3$Pro$^1$, D-(pF)Phe$^2$, D-Trp$^{3,6}$] LHRH

[Ac-D-(pCl)Phe$^1$D-(pCl)Phe$^2$, D-Trp$^3$, D-Arg$^6$, D-Arg$^{10}$] LHRH and

[Ac-D-Nal(2)$^1$D-(pCl)Phe$^2$, D-Trp$^3$, D-hArg(Et$_2$)$^6$, D-Arg$^{10}$] LHRH.

35. The method according to claim 28 wherein the therapeutically effective amount of the first LHRH analog and the therapeutically effective amount of the second LHRH analog are sufficient to maintain blood serum concentrations of testosterone at about 2 to 10 nmol/l, FSH at about 2 to 10 IU/l, and LH at about 2 to 10 IU/l.

36. The method according to claim 35 wherein the LHRH analogs are administered by topical application.

37. The method according to claim 36 wherein the LHRH analog is applied to the skin of the armpit region.

38. The method according to claim 35 wherein the LHRH analogs are administered transdermally.

39. The method according to claim 35 wherein the LHRH analogs are administered transmucosally.

40. The method according to claim 35 wherein the LHRH analogs are administered by subcutaneous or intramuscular injection.

41. The method according to claim 35 wherein the LHRH analogs are administered by subdermal implant.

42. The method according to claim 35 wherein the LHRH analogs are administered orally.

43. A tablet for oral administration of LHRH analogs comprising:

a) a top layer comprising one or more non-steroidal, polypeptide analogs of LHRH capable of suppressing testosterone formation in patients in the active phases of male pattern baldness and a pharmaceutically acceptable carrier thereof;

b) a bottom layer, adjacent to said top layer, comprised of material capable of expanding upon contact with water; and c) a water insoluble, water semipermeable membrane, covering the top and bottom layers; said membrane having an opening of a size sufficient to permit water to enter the tablet and to permit release of LHRH analog from the tablet top layer.

* * * * *